(12) United States Patent
Schafer et al.

(10) Patent No.: US 11,357,775 B2
(45) Date of Patent: Jun. 14, 2022

(54) COMBINATION THERAPIES COMPRISING APREMILAST AND TYK2 INHIBITORS

(71) Applicant: Celgene Corporation, Summit, NJ (US)

(72) Inventors: Peter Henry Schafer, Belle Mead, NJ (US); Robert Plenge, Wellesley, MA (US); Mary Adams, Mountain Lakes, NJ (US); Lisa Beebe, Acton, MA (US); Gilles Buchwalter, Cambridge, MA (US); Tiffany Carr, Cambridge, MA (US); Te-chen Tzeng, Shrewsbury, MA (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 16/398,569

(22) Filed: Apr. 30, 2019

(65) Prior Publication Data
US 2020/0345731 A1    Nov. 5, 2020

(51) Int. Cl.
*A61K 31/501* (2006.01)
*A61P 17/06* (2006.01)
*A61K 9/00* (2006.01)

(52) U.S. Cl.
CPC .......... *A61K 31/501* (2013.01); *A61K 9/0053* (2013.01); *A61P 17/06* (2018.01)

(58) Field of Classification Search
CPC combination set(s) only.
See application file for complete search history.

(56) References Cited

U.S. PATENT DOCUMENTS

| | | | |
|---|---|---|---|
| 6,962,940 B2 * | 11/2005 | Muller | A61P 17/06 514/417 |
| 7,208,516 B2 | 4/2007 | Muller et al. | |
| 7,427,638 B2 | 9/2008 | Muller et al. | |
| 7,659,302 B2 | 2/2010 | Muller et al. | |
| 7,893,101 B2 | 2/2011 | Muller et al. | |
| 8,455,536 B2 | 6/2013 | Muller et al. | |
| 8,802,717 B2 | 8/2014 | Muller et al. | |
| 9,018,243 B2 | 4/2015 | Muller et al. | |
| 9,724,330 B2 | 8/2017 | Muller et al. | |
| 9,872,854 B2 | 1/2018 | Day | |
| 10,092,541 B2 | 10/2018 | Day | |
| RE47,929 E | 4/2020 | Moslin et al. | |
| 2016/0045475 A1 | 2/2016 | Day | |
| 2018/0258086 A1 | 9/2018 | Greenwood et al. | |

FOREIGN PATENT DOCUMENTS

WO    2015/123453 A1    8/2015

OTHER PUBLICATIONS

Zerilli (Apremilast (otezla): A New oral treatment for Adults With Psoriasis and Psoriatic Arthritis, Drug Forecast, vol. 40 No. 8 • Aug. 2015, pp. 495-500).*
Papp (Phase 2 Trial of Selective Tyrosine Kinase 2 Inhibition in Psoriasis, The New England Journal of Medicine, 379;14, Oct. 2018, pp. 1313-1321).*

* cited by examiner

*Primary Examiner* — Kathrien A Cruz
(74) *Attorney, Agent, or Firm* — McCarter & English, LLP; Basil S. Krikelis; Michael J. DeGrazia

(57) ABSTRACT

Provided herein are methods of treating diseases and disorder responsive to the inhibition of PDE4 comprising administering apremilast and a Tyk2 inhibitor to a subject. Also provided herein are pharmaceutical compositions comprising apremilast and a Tyk2 inhibitor.

20 Claims, 17 Drawing Sheets

COMBINATION THERAPIES COMPRISING APREMILAST AND TYK2 INHIBITORS

BACKGROUND

N-[2-[(1S)-1-(3-ethoxy-4-methoxyphenyl)-2-(methylsulfonyl)ethyl]-2,3-dihydro-1,3-dioxo-1H-isoindol-4-0]acetamide (apremilast), marketed as Otezla®, is a phosphodiesterase type 4 (PDE4) inhibitor currently approved for treating both moderate to severe plaque psoriasis and active psoriatic arthritis. PDE4 inhibition by apremilast elevates cyclic adenosine monophosphate (cAMP) levels in immune cells. This in turn down-regulates inflammatory responses by reducing the expression of pro-inflammatory mediators such as TNF-α, IL-23, IL-17, and other inflammatory cytokines, and increases the production of anti-inflammatory mediators. Studies have shown that a 75% reduction in plaque psoriasis is achievable in some patients in as little as just over 4 months of treatment.

Tyrosine kinase 2 (Tyk2), an intracellular signaling enzyme, activates signal transducer and activator of transcription (STAT)-dependent gene expression and functional responses of IL-12, IL-23, and type I and III interferon receptors. Amongst other conditions, tyrosine kinase inhibitors (TKIs) have recently gained attention as effective agents for treating psoriasis and related conditions. The TKI inhibitor BMS-986165, for example, recently showed positive results in phase 2 clinical trials in subjects with moderate to severe plaque psoriasis. See Kim Papp, M.D., Phase 2 Trial of Selective Tyrosine Kinase 2 Inhibition in Psoriasis, The New England Journal of Medicine, Sep. 12, 2018.

SUMMARY

It has now been found that the combination of apremilast and the Tyk2 inhibitor 6-(cyclopropanecarboxamido)-4-((2-methoxy-3-(1-methyl-1H-1,2,4-triazol-3-yl)phenyl)amino)-N-(methyl-d3)pyridazine-3-carboxamide (BMS-986165) synergistically reduces pro-inflammatory cytokines expressed in a whole blood assay under conditions that stimulate Th17 cells. For example, there was over a 2-fold increase in the inhibition of IL-17F expression using the combination of 0.01 µM BMS-986165 and 1 µM apremilast when compared to the use of each drug alone. See e.g., Table 5 in the Exemplification section. Similar results were seen at 0.1 µM concentrations of BMS-986165 with 1 µM apremilast. See e.g., Table 5. The combination of BMS-986165 with 1 µM apremilast also reduced cytokine expression for IL-17A and IL-22 at values of 2-fold or greater over the use of each drug alone. See e.g., Table 5.

It was also found that the combination of apremilast and BMS-986165 elicit complementary effects against certain pro-inflammatory cytokines. BMS-986165, for example, increased TNF-α and GM-CSF cytokine in whole blood assay, while apremilast inhibited the production of these cytokines. See e.g., Table 5 where the % control for 1 µM apremilast was 10.7 and the % control for 0.01 µM BMS-986165 was 143.1 against TNF-α. When administered in combination, however, apremilast corrected the deficiency of BMS-986165 thereby producing a complementary effect of 13.5% inhibition against TNF-α. See e.g., Table 5. This trend was also established at 0.1 µM concentrations of BMS-986165 and against cytokine GM-CSF. See e.g., Table 5. These results illustrate the synergistic and complementary pharmacological effects of BMS-986165 and apremilast.

In addition to whole blood assay, the combination of BMS-986165 and apremilast elicit complementary effects against certain pro-inflammatory cytokines in LPS stimulated PBMCs as well. BMS-986165 increased IL-23, IL-12 and TNF-α, while apremilast inhibited the production of these cytokines. See e.g., Table 6 in the Exemplification section. These results further support the advantage of combining BMS-986165 and apremilast in treatment of Th17 related diseases.

Provided herein, therefore are methods of treating diseases or disorders responsive to the inhibition of PDE4 in a subject using an effective amount of apremilast, or a pharmaceutically acceptable salt thereof, and an effective amount of a Tyk2 inhibitor such as BMS-986165. Such diseases and disorders include e.g., inflammatory diseases such as psoriasis, psoriatic arthritis, and ulcerative colitis.

Also provided herein are pharmaceutical compositions comprising an effective amount of apremilast, or a pharmaceutically acceptable salt thereof, and an effective amount of a Tyk2 inhibitor such as BMS-986165.

or anti-CD3/anti-CD28, IL-1β, IL-6 and IL-23 (Th17) stimulated whole blood—TruCulture® tube assay.

Figure 11:
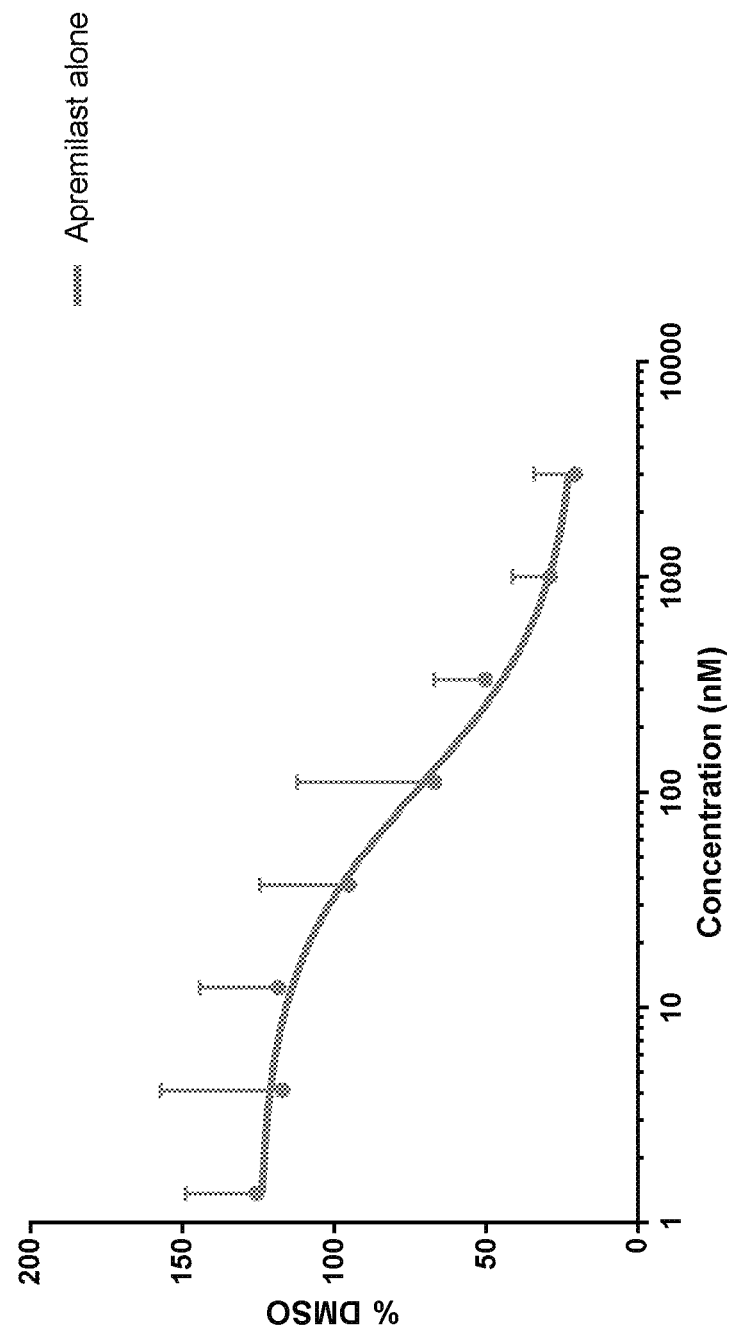

FIG. 11 illustrates interleukin-23 (IL-23) cytokine production by apremilast in Lipopolysaccharide (LPS) stimulated peripheral blood mononuclear cells (PBMCs).

Figure 12:
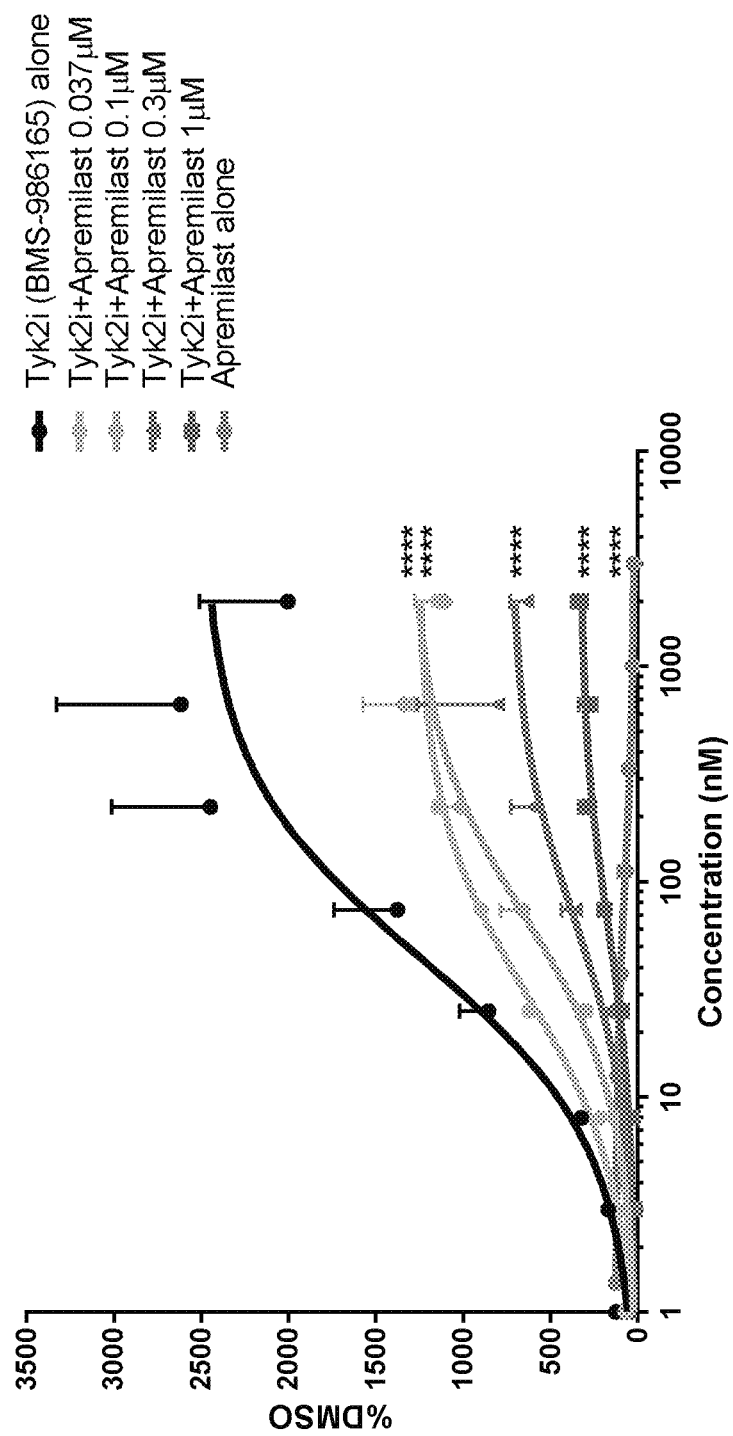

FIG. 12 illustrates interleukin-23 (IL-23) cytokine production by apremilast and Tyk2i (BMS-986165) in LPS stimulated PBMCs.

Figure 13:
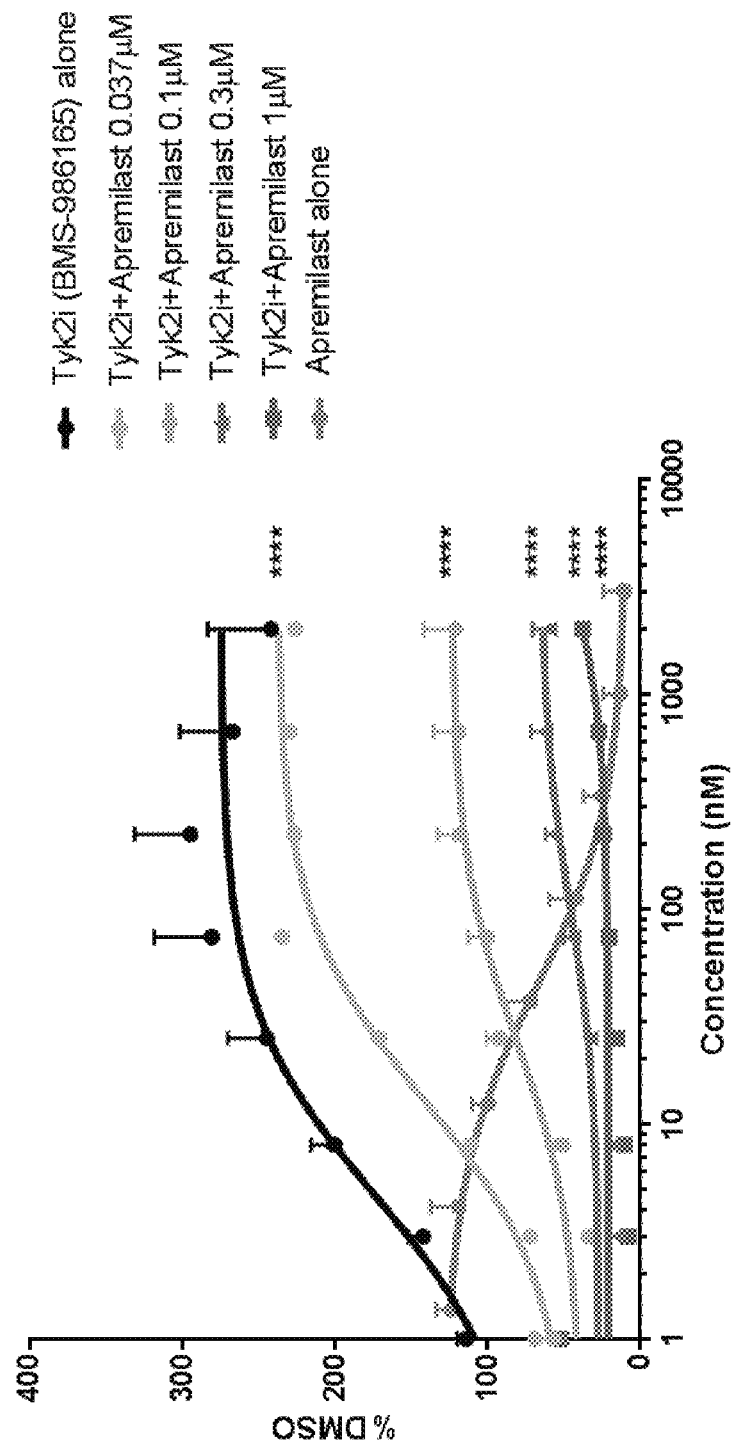

FIG. 13 illustrates interleukin-12p40 (IL-12p40) cytokine production by apremilast and Tyk2i (BMS-986165) in LPS stimulated PBMCs.

Figure 14:
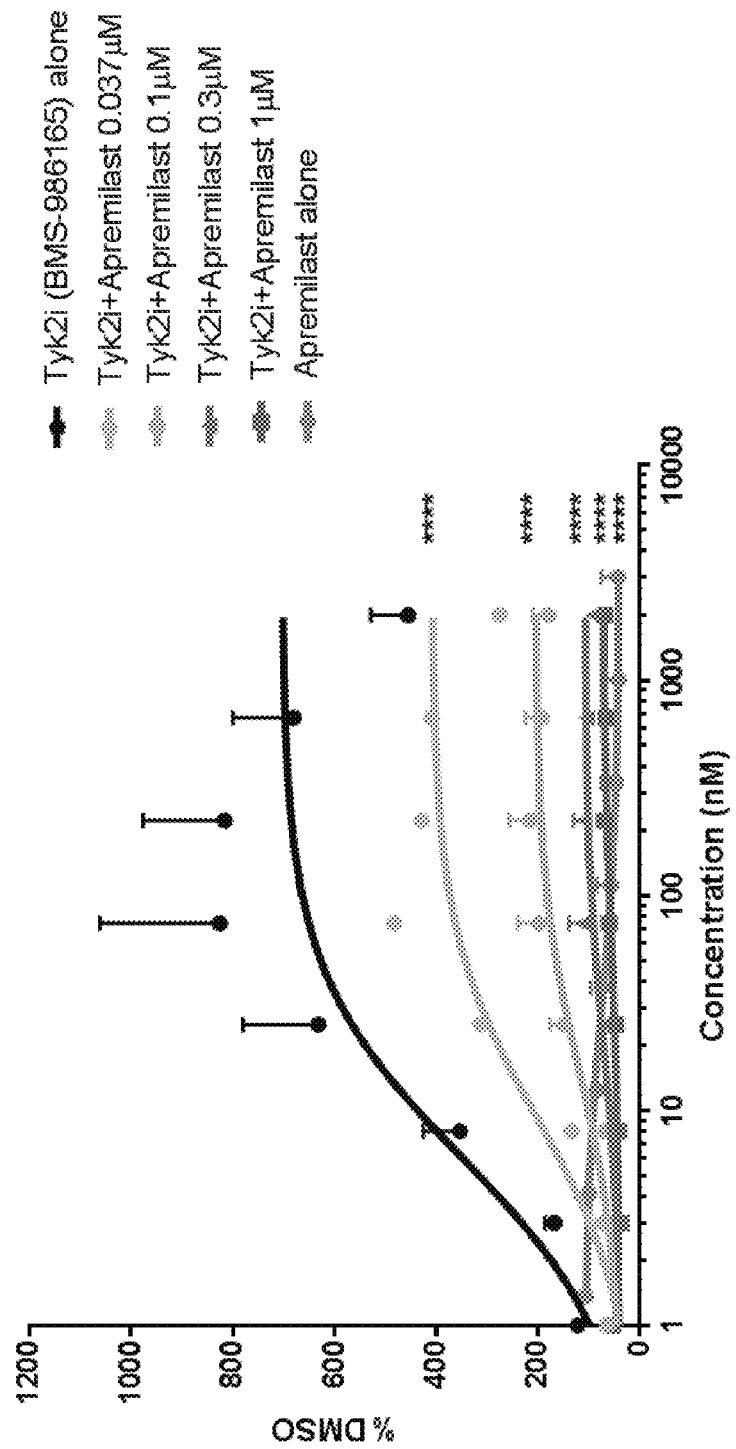

FIG. 14 illustrates interleukin-12p70 (IL-12p70) cytokine production by apremilast and Tyk2i (BMS-986165) in LPS stimulated PBMCs.

Figure 15:
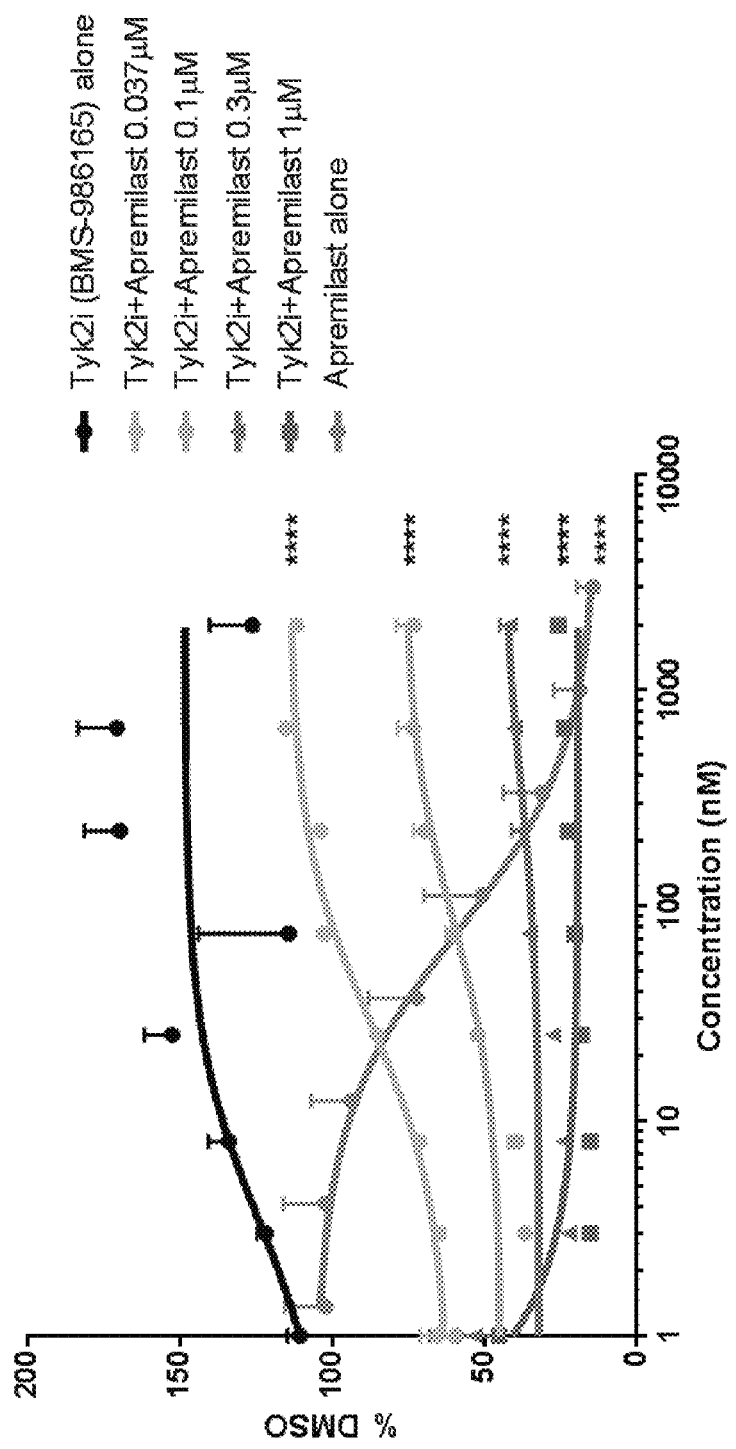

FIG. 15 illustrates tumor necrosis factor alpha (TNF-α) cytokine production by apremilast and Tyk2i (BMS-986165) in LPS stimulated PBMCs.

Figure 16:
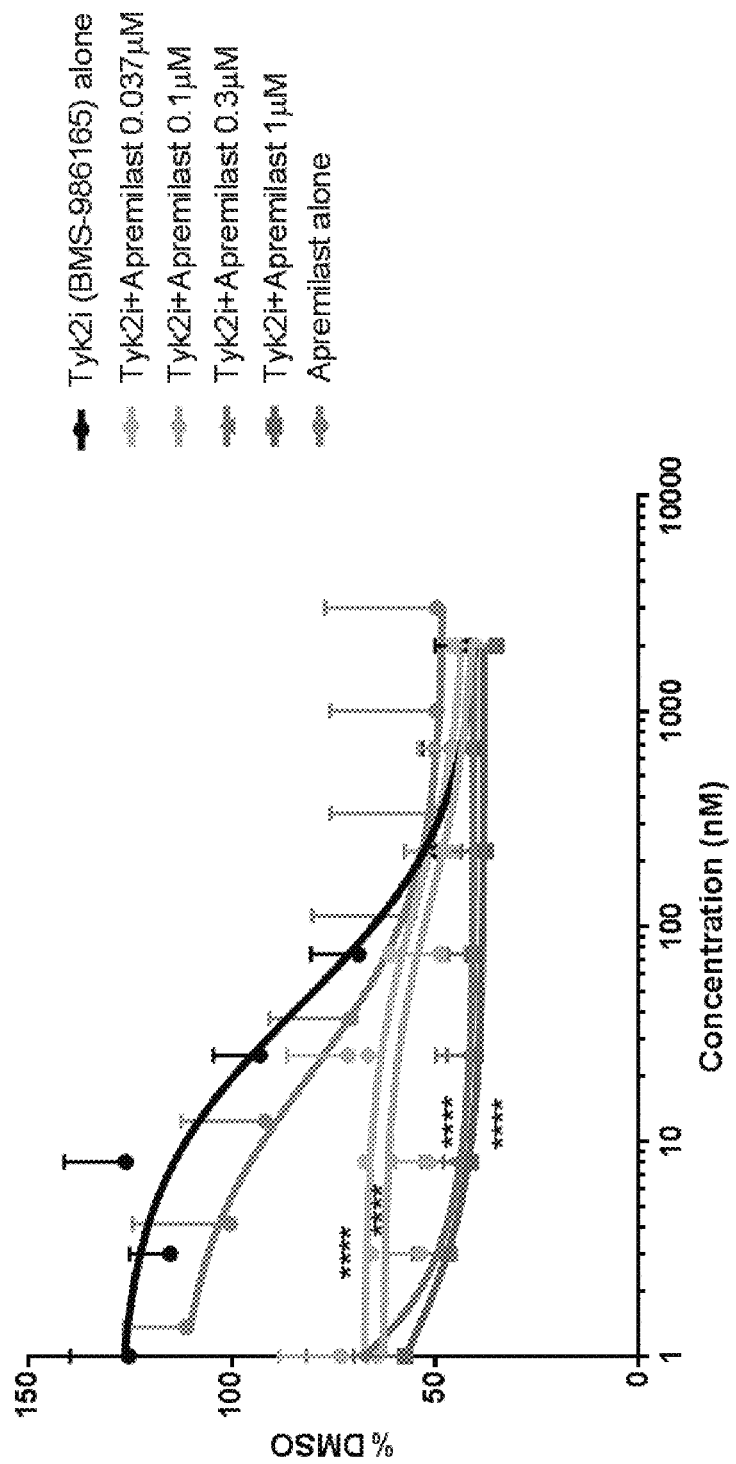

FIG. 16 illustrates interferon gamma (IFN-γ) cytokine production by apremilast and Tyk2i (BMS-986165) in LPS stimulated PBMCs.

Figure 17:
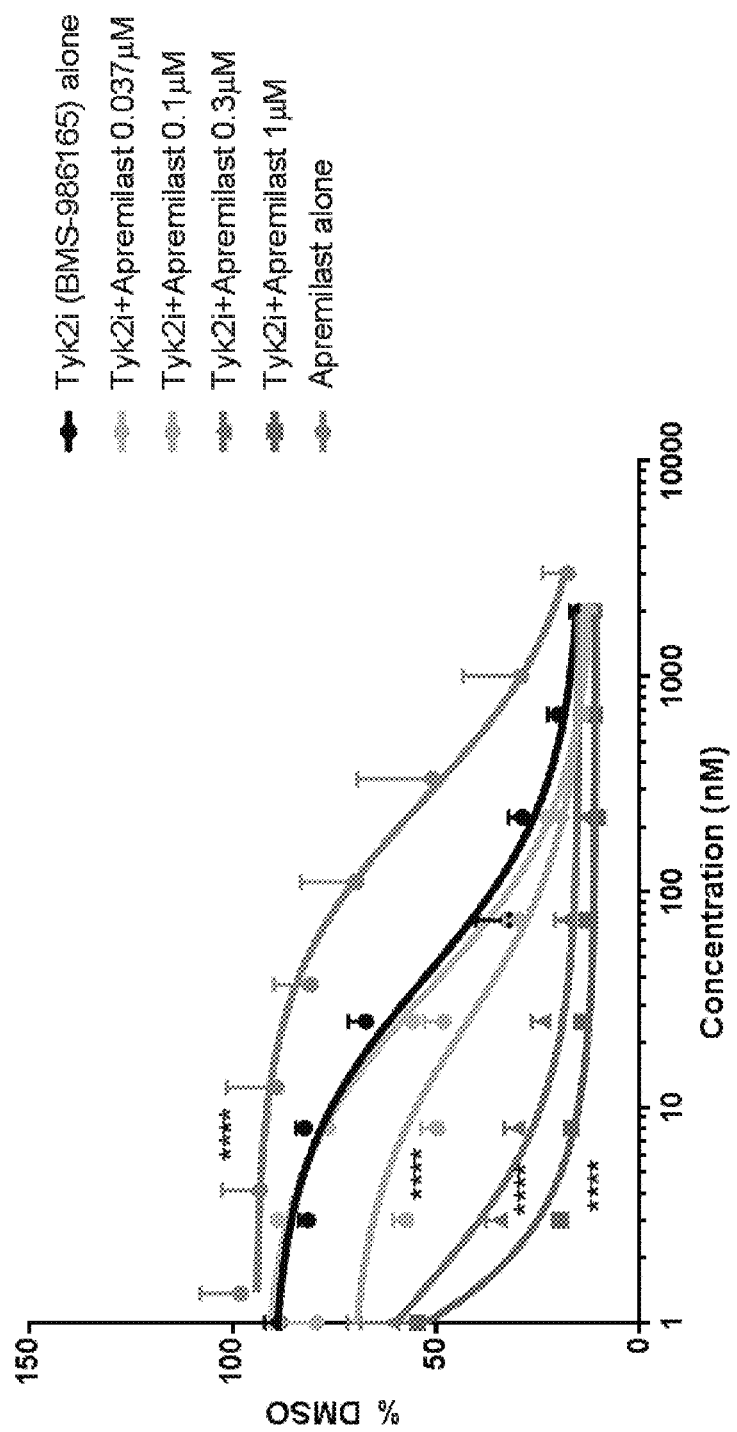

FIG. 17 illustrates monocyte chemoattractant protein-1 (MCP-1) cytokine production by apremilast and Tyk2i (BMS-986165) in LPS stimulated PBMCs.

DETAILED DESCRIPTION

In a first embodiment, provided herein are methods for treating a disease or disorder responsive to the inhibition of cyclic nucleotide phosphodiesterase isoenzyme IV (PDE4), the method comprising administering to a subject an effective amount of N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast), or a pharmaceutically acceptable salt thereof, and an effective amount of a Tyk2 inhibitor.

Alternatively, as part of a first embodiment, provided is the use of an effective amount of N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast), or a pharmaceutically acceptable salt thereof, and an effective amount of a Tyk2 inhibitor, in the manufacture of a medicament for treating a disease or disorder responsive to the inhibition of cyclic nucleotide phosphodiesterase isoenzyme IV (PDE4).

In another alternative, as a part of a first embodiment, provided is an effective amount of N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast), or a pharmaceutically acceptable salt thereof, and an effective amount of a Tyk2 inhibitor, for use in treating a disease or disorder responsive to the inhibition of cyclic nucleotide phosphodiesterase isoenzyme IV (PDE4).

1. Definitions

N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast) is disclosed in U.S. Pat. No. 6,962,940, the contents of which are incorporated herein by reference, and refers to the compound having the following chemical structure:

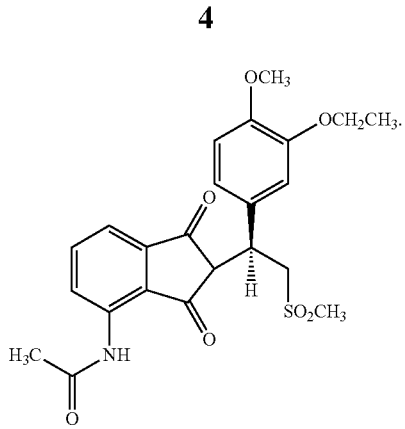

Apremilast has a chiral center designated as (S) in the chemical structure and name. As used herein, this designation means that apremilast is optically enriched as the (S) enantiomer at this position in an amount of at least 80%, 90%, 95%, 98%, 99%, or 99.9% relative to the corresponding (R) enantiomer. Thus, when apremilast is referred to herein as being stereomerically or enantiomerically pure at a specified amount, it means that the (S) enantiomer is enriched in that amount. For example, N-[2-[(1S)-1-(3-ethoxy-4-methoxyphenyl)-2-(methylsulfonyl)ethyl]-2,3-dihydro-1,3-dioxo-1H-isoindol-4-yl]acetamide that is at least 95% stereomerically pure means that the compound contains greater than or equal to 95% of the (S) enantiomer and 5% or less of the (R) enantiomer.

Unless otherwise indicated, the administrations described herein include administering apremilast prior to, concurrently with, or after administration of the Tyk2 inhibitor described herein. Thus, simultaneous administration is not necessary for therapeutic purposes. In one aspect, apremilast and a disclosed Tyk2 inhibitor are administered together. In another aspect, apremilast and a disclosed Tyk2 inhibitor are administered at different times on the same day. In another aspect, apremilast and a disclosed Tyk2 inhibitor are administered at different times as separate tablets or capsules. In another aspect, apremilast and a disclosed Tyk2 inhibitor are administered in a fixed dose combination in the same tablet or capsule.

The terms "treatment," "treat," and "treating" refer to reversing, alleviating, or inhibiting the progress of a disease or disorder responsive to the inhibition of PDE4, or one or more symptoms thereof, as described herein.

The term "subject" means an animal, such as a mammal, and such as a human. The terms "subject" and "patient" may be used interchangeably.

The term "effective amount" or "therapeutically effective amount" refers to an amount of a compound described herein that will elicit a biological or medical response of a subject e.g., a dosage of between 0.001-100 mg/kg body weight/day.

The term "pharmaceutically acceptable carrier" refers to a non-toxic carrier, adjuvant, or vehicle that does not adversely affect the pharmacological activity of the compound with which it is formulated, and which is also safe for human use. Pharmaceutically acceptable carriers, adjuvants or vehicles that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

The term "pharmaceutically acceptable salts" refer to salts prepared from pharmaceutically acceptable non-toxic acids or bases including inorganic acids and bases and organic acids and bases. Suitable pharmaceutically acceptable base addition salts for the compounds described herein include, but are not limited to include metallic salts made from aluminum, calcium, lithium, magnesium, potassium, sodium and zinc or organic salts made from lysine, N,N'-dibenzylethylenediamine, chloroprocaine, choline, diethanolamine, ethylene diamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methane sulfonic, mucic, nitric, pamoic, pantothenic, phenylacetic, phosphoric, propionic, salicylic, stearic, succinic, sulfanilic, sulfuric, tartaric acid, and p-toluenesulfonic acid.

"Crystalline" refers to a solid form of a compound wherein there exists long-range atomic order in the positions of the atoms. The crystalline nature of a solid can be confirmed, for example, by examination of the X-ray powder diffraction pattern. A "single crystalline form" means that the recited compound, i.e., N-[2-[(1S)-1-(3-ethoxy-4-methoxyphenyl)-2-(methylsulfonyl)ethyl]-2,3-dihydro-1,3-dioxo-1H-isoindol-4-yl]acetamide, is present as a single crystal or a plurality of crystals in which each crystal has the same crystal form (e.g., crystalline Form B). When the crystal form is defined as a specified percentage of one particular single crystalline form of the compound, the remainder is made up of amorphous form and/or crystalline forms other than the one or more particular forms that are specified. In one aspect, e.g., a disclosed crystalline form is at least 80% a single crystalline form, at least 90% a single crystalline form, at least 95% a single crystalline form, or at least 99% a single crystalline form by weight. Percent by weight of a particular crystal form is determined by the weight of the particular crystal form divided by the sum weight of the particular crystal, plus the weight of the other crystal forms present plus the weight of amorphous form present multiplied by 100%.

The term "amorphous" refers to a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

The 2-theta values of the X-ray powder diffraction patterns for the crystalline forms described herein may vary slightly from one instrument to another and also depending on variations in sample preparation and batch to batch variation due to factors such as temperature variation, sample displacement, and the presence or absence of an internal standard. Therefore, unless otherwise defined, the XRPD patterns/assignments recited herein are not to be construed as absolute and can vary ±0.2 degrees. It is well known in the art that this variability will account for the above factors without hindering the unequivocal identification of a crystal form.

2. Tyk2 Inhibitors

Tyk2 inhibitors used in the disclosed methods and compositions include compounds which block the action of tyrosine kinase 2, a non-receptor tyrosine-protein kinase encoded by the Tyk2 gene.

In a second embodiment, the disclosed Tyk2 inhibitors include, but are not limited to, those described in Xingrui He et al., Expert Opinion on Therapeutics Patents 2019, Vol. 29, No. 2, 137-149, the entire contents of which are incorporated herein by reference.

In a third embodiment, the disclosed Tyk2 inhibitors may be selected from those having the formula:

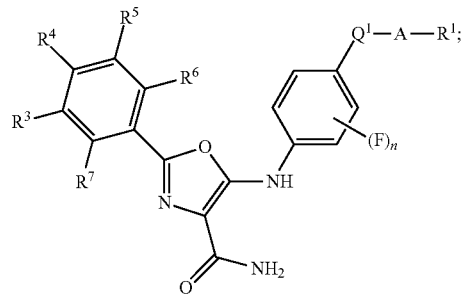

or a pharmaceutically acceptable salt thereof, wherein the variables are as described in WO 2015/032423, the entire contents of which are incorporated herein by reference. Exemplary compounds having this formula as part of the third embodiment include, but are not limited to, those having the formula:

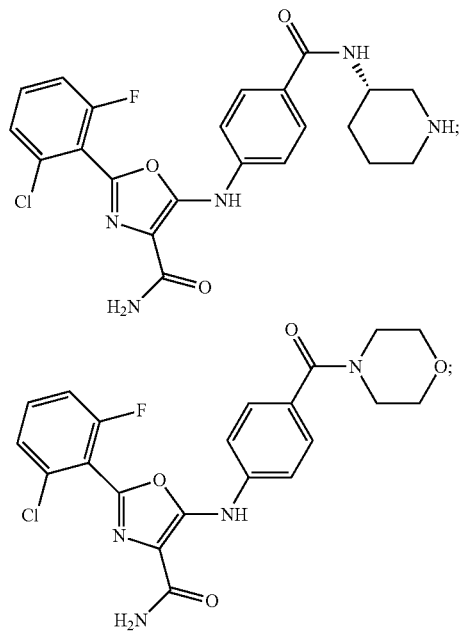

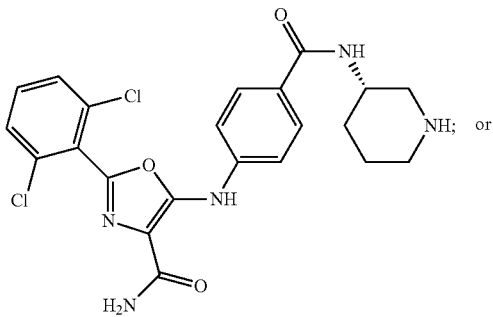

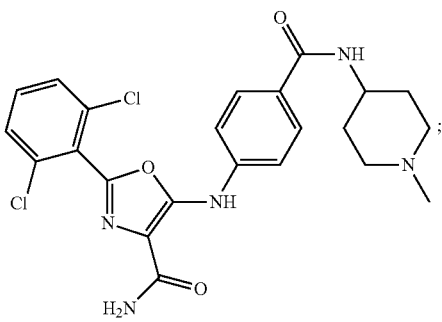

or a pharmaceutically acceptable salt thereof. Other Tyk2 inhibitors as part of the third embodiment include those in WO 2008/139161, and WO 2010/055304, the entire contents of each of which are incorporated herein by reference.

In a fourth embodiment, the disclosed Tyk2 inhibitors may be selected from those having the formula:

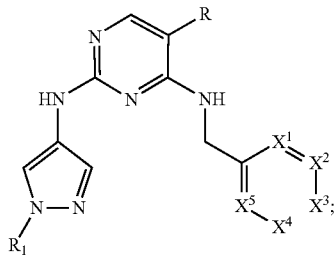

or a pharmaceutically acceptable salt thereof, wherein the variables are as described in WO 2013/174895, the entire contents of which are incorporated herein by reference. Exemplary compounds having this formula as part of the fourth embodiment include, but are not limited to, those having the formula:

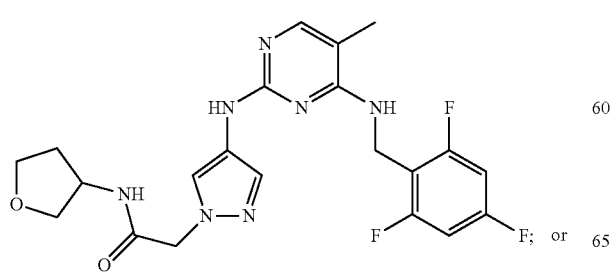

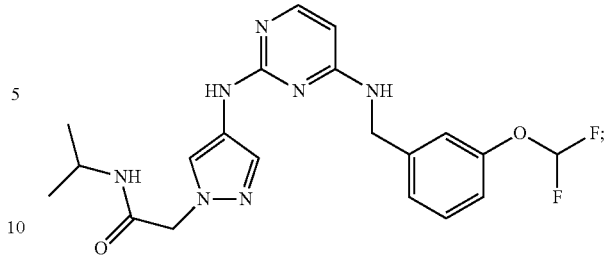

or a pharmaceutically acceptable salt thereof. Other Tyk2 inhibitors include those in WO 2012/062704, the entire contents of which are incorporated herein by reference.

In a fifth embodiment, the disclosed Tyk2 inhibitors may be selected from those having the formula:

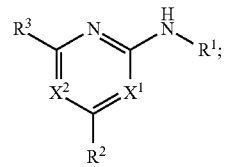

or a pharmaceutically acceptable salt thereof, wherein the variables are as described in WO 2012/062704, the entire contents of which are incorporated herein by reference.

In a sixth embodiment, the disclosed Tyk2 inhibitors may be selected from those having the formulae:

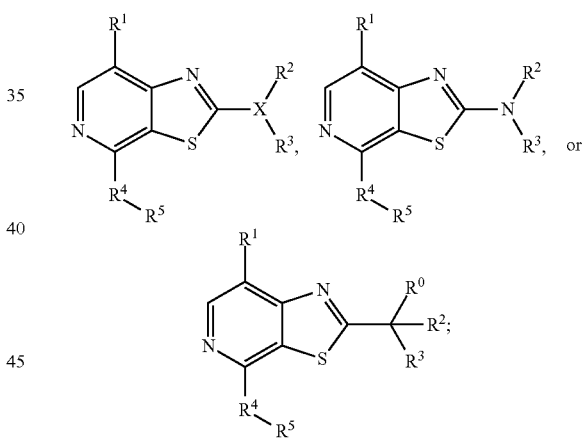

or a pharmaceutically acceptable salt thereof, wherein the variables are as described in WO 2015/091584, the entire contents of which are incorporated herein by reference. Exemplary compounds having this formula as part of the sixth embodiment include, but are not limited to, those having the formula:

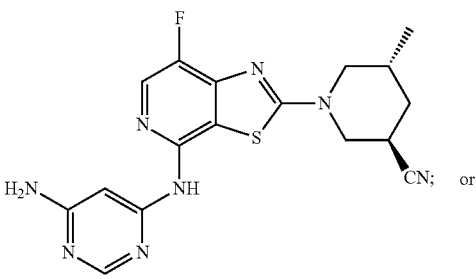

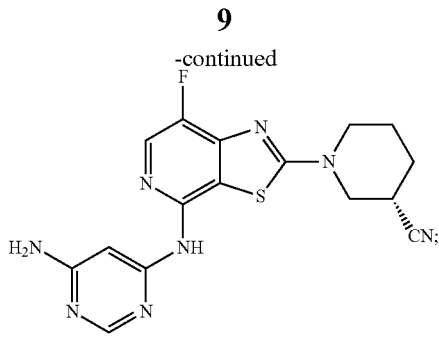

or a pharmaceutically acceptable salt thereof.

In a seventh embodiment, the disclosed Tyk2 inhibitors may be selected from those having the formula:

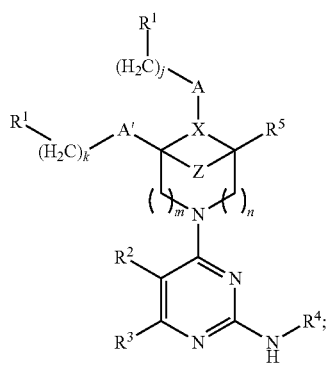

or a pharmaceutically acceptable salt thereof, wherein the variables are as described in WO 2016/027195, the entire contents of which are incorporated herein by reference. Exemplary compounds having this formula as part of the seventh embodiment include, but are not limited to, those having the formula:

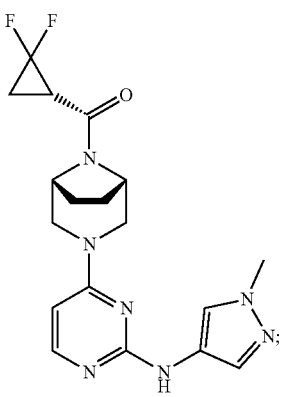

or a pharmaceutically acceptable salt thereof.

In an eighth embodiment, the disclosed Tyk2 inhibitors may be selected from those having the formula:

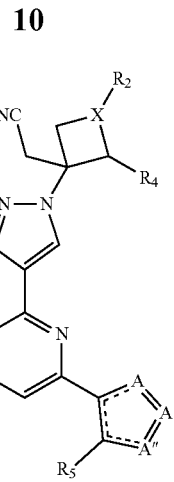

or a pharmaceutically acceptable salt thereof, wherein the variables are as described in US 2017/0240552, the entire contents of which are incorporated herein by reference. Exemplary compounds having this formula as part of the eighth embodiment include, but are not limited to, those having the formula:

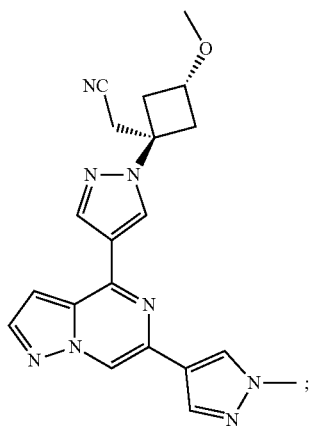 [SMILES: CO[C@H]1C[C@](CC#N)(n2cc(-c3nc(-c4cnn(C)c4)cn4nccc34)cn2)C1]

or a pharmaceutically acceptable salt thereof.

In a ninth embodiment, the disclosed Tyk2 inhibitors may be selected from those having the formula:

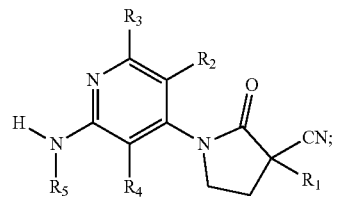

or a pharmaceutically acceptable salt thereof, wherein the variables are as described in WO 2015/016206, the entire contents of which are incorporated herein by reference.

In a tenth embodiment, the disclosed Tyk2 inhibitors may be selected from those having the formula:

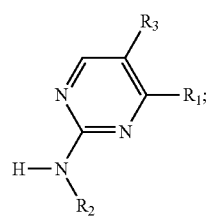

or a pharmaceutically acceptable salt thereof, wherein the variables are as described in WO 2013/146963, the entire contents of which are incorporated herein by reference.

In an eleventh embodiment, the disclosed Tyk2 inhibitors may be selected from those having the formula:

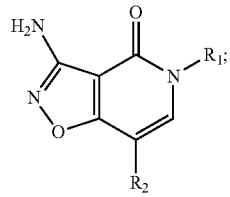

or a pharmaceutically acceptable salt thereof, wherein the variables are as described in WO 2016/047678, the entire contents of which are incorporated herein by reference.

In a twelfth embodiment, the disclosed Tyk2 inhibitors may be selected from those described in US 2015/0299139; WO 2015/069310; U.S. Pat. No. 9,505,748; WO 2018/0162889; US 2013/0178478; or WO 2015/123453, the entire contents of each of which are incorporated herein by reference.

In a thirteenth embodiment, the disclosed Tyk2 inhibitors may be selected from those having the formula:

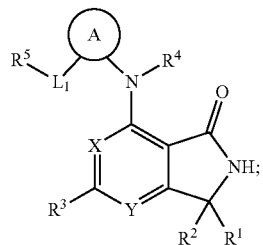

or a pharmaceutically acceptable salt thereof, wherein the variables are as described in WO 2015/131080 or WO 2016/138352, the entire contents of which are incorporated herein by reference.

In a fourteenth embodiment, the disclosed Tyk2 inhibitors may be selected from those having the formula:

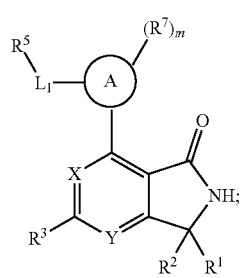

or a pharmaceutically acceptable salt thereof, wherein the variables are as described in WO 2017/040757, the entire contents of which are incorporated herein by reference.

In a fifteenth embodiment, the disclosed Tyk2 inhibitors may be selected from those having the formula:

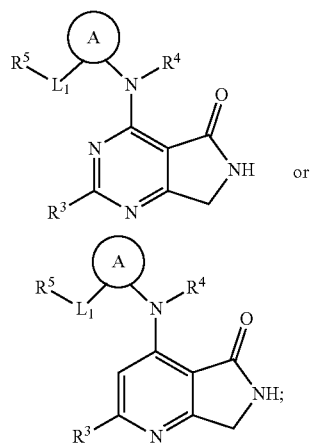

or a pharmaceutically acceptable salt thereof, wherein the variables are as described in WO 2015/131080, WO 2016/138352, and WO 2017/040757, the entire contents of which are incorporated herein by reference.

In a sixteenth embodiment, the disclosed Tyk2 inhibitors may be selected from those having the formula:

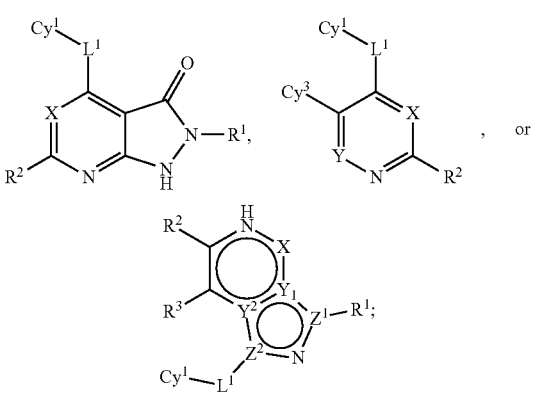

or a pharmaceutically acceptable salt thereof, wherein the variables are as described in WO 2018/071794, the entire contents of which are incorporated herein by reference.

In a seventeenth embodiment, the disclosed Tyk2 inhibitors may be selected from those having the formula:

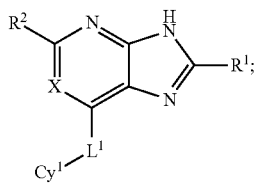

or a pharmaceutically acceptable salt thereof, wherein the variables are as described in WO 2018/075937, the entire contents of which are incorporated herein by reference.

In an eighteenth embodiment, the disclosed Tyk2 inhibitors may be selected from those having the formula:

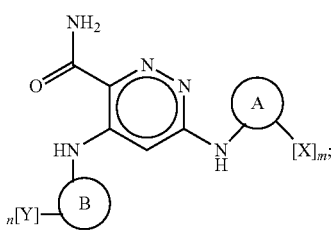

or a pharmaceutically acceptable salt thereof, wherein the variables are as described in US 2013/0178478, the entire contents of which are incorporated herein by reference.

In a nineteenth embodiment, the disclosed Tyk2 inhibitors may be selected from those having the formula:

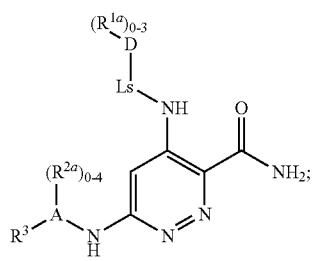

or a pharmaceutically acceptable salt thereof, wherein the variables are as described in WO 2015/123453, the entire contents of which are incorporated herein by reference.

In a twentieth embodiment, the disclosed Tyk2 inhibitors may be selected from those having the formula:

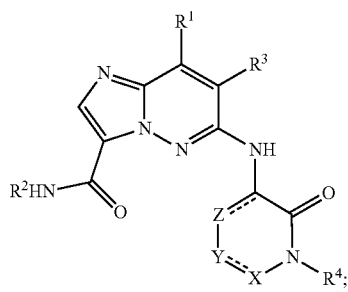

or a pharmaceutically acceptable salt thereof, wherein the variables are as described in WO 2015/089143, the entire contents of which are incorporated herein by reference.

In a twenty-first embodiment, the disclosed Tyk2 inhibitors may be selected from those having the formula:

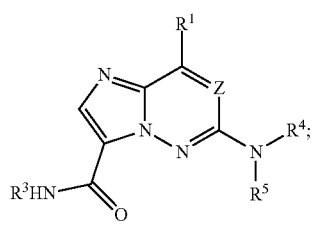

or a pharmaceutically acceptable salt thereof, wherein the variables are as described in WO 2015/089143, the entire contents of which are incorporated herein by reference.

In a twenty-second embodiment, the disclosed Tyk2 inhibitors may be selected from those having the formula:

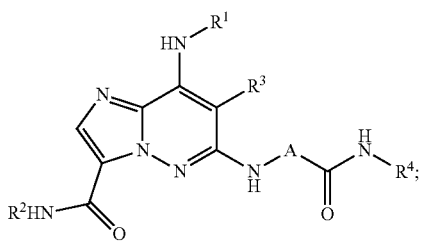

or a pharmaceutically acceptable salt thereof, wherein the variables are as described in WO 2018/067432, the entire contents of which are incorporated herein by reference.

In a twenty-third embodiment, the disclosed Tyk2 inhibitors may be selected from those having the formula:

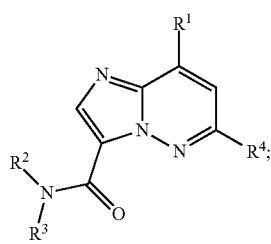

or a pharmaceutically acceptable salt thereof, wherein the variables are as described in WO 2018/093968, the entire contents of which are incorporated herein by reference.

In a twenty-fourth embodiment, the disclosed Tyk2 inhibitors may be selected from those having the formula:

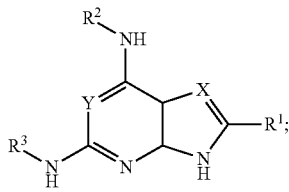

or a pharmaceutically acceptable salt thereof, wherein the variables are as described in WO 2018/081488, the entire contents of which are incorporated herein by reference.

In a twenty-fifth embodiment, the disclosed Tyk2 inhibitors may be selected from those having the formula:

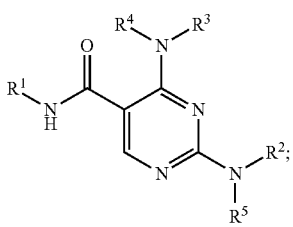

or a pharmaceutically acceptable salt thereof, wherein
$R^1$ is $C_{1-3}$alkyl optionally substituted by 0-7 $R^{1a}$;
$R^{1a}$ at each occurrence is independently hydrogen, deuterium, F, Cl, Br, $CF_3$ or CN;

R² is C₁₋₆alkyl or —(CH₂)ᵣ-3-14 membered carbocycle, each group substituted with 0-4 R²ᵃ;

R²ᵃ at each occurrence is independently hydrogen, =O, halo, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, NRᵇS(O)ₚRᶜ, —S(O)ₚRᶜ, C₁₋₆ alkyl substituted with 0-3 Rᵃ, C₁₋₆haloalkyl, C₂₋₆ alkenyl substituted with 0-3 Rᵃ, C₂₋₆ alkynyl substituted with 0-3 Rᵃ, —(CH₂)ᵣ-3-14 membered carbocycle substituted with 0-1 Rᵃ or a —(CH₂)ᵣ-5-7 membered heterocycle comprising carbon atoms or 1-4 heteroatoms selected from N, O, and S(O)ₚ substituted with 0-2 Rᵃ;

R³ is C₃₋₁₀ cycloalkyl, C₆₋₁₀ aryl, or a 5-10 membered heterocycle containing 1-4 heteroatoms selected from N, O, and S, each group substituted with 0-4 R³ᵃ;

R³ᵃ at each occurrence is independently hydrogen, =O, halo, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₂₋₆ alkenyl substituted with 0-3 Rᵃ, C₂₋₆ alkynyl substituted with 0-3 Rᵃ, C₁₋₆ haloalkyl, —(CH₂)ᵣ-3-14 membered carbocycle substituted with 0-3 Rᵃ or a —(CH₂)ᵣ-5-10 membered heterocycle comprising carbon atoms and 1-4 heteroatoms selected from N, O, and S(O)ₚ substituted with 0-3 Rᵃ;

or two R³ᵃ, together with the atoms to which they are attached, combine to form a fused ring wherein said ring is selected from phenyl and a 5-7 membered heterocycle comprising carbon atoms and 1-4 heteroatoms selected from N, S or O said fused ring further substituted by Rᵃ¹;

R⁴ and R⁵ are independently hydrogen, C₁₋₄ alkyl substituted with 0-1 Rᶠ, (CH₂)ᵣ-phenyl substituted with 0-3 Rᵈ, or a —(CH₂)-5-7 membered heterocycle comprising carbon atoms and 1-4 heteroatoms selected from N, O, and S(O)ₚ;

R¹¹ at each occurrence is independently hydrogen, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ, or —(CH₂)ᵣ-5-7 membered heterocycle comprising carbon atoms and 1-4 heteroatoms selected from N, O, and S(O)ₚ substituted with 0-3 Rᵈ;

Rᵃ and Rᵃ¹ at each occurrence are independently hydrogen, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, C₂₋₆ alkenyl substituted with 0-3 Rᵃ, C₂₋₆ alkynyl substituted with 0-3 Rᵃ, —(CH₂)ᵣ-3-14 membered carbocycle or —(CH₂)ᵣ-5-7 membered heterocycle comprising carbon atoms and 1-4 heteroatoms selected from N, O, and S(O)ₚ substituted with 0-3 Rᶠ;

Rᵇ at each occurrence is independently hydrogen, C₁₋₆ alkyl substituted with 0-3 Rᵈ, C₁₋₆haloalkyl, C₃₋₆cycloalkyl substituted with 0-2 Rᵈ, or —(CH₂)ᵣ-5-7 membered heterocycle comprising carbon atoms and 1-4 heteroatoms selected from N, O, and S(O)ₚ substituted with 0-3 Rᶠ or (CH₂)ᵣ-phenyl substituted with 0-3 Rᵈ;

Rᶜ is C₁₋₆ alkyl substituted with 0-3 Rᶠ, (CH₂)ᵣ—C₃₋₆ cycloalkyl substituted with 0-3 Rᶠ, (CH₂)ᵣ-phenyl substituted with 0-3 Rᶠ; or Rᵈ at each occurrence is independently hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl, or (CH₂)ᵣ-phenyl substituted with 0-3 Rᶠ;

Rᵉ at each occurrence is independently selected from hydrogen, C₁₋₆ alkyl, C₃₋₆ cycloalkyl, and (CH₂)ᵣ-phenyl substituted with 0-3 Rᶠ;

Rᶠ independently at each occurrence is hydrogen, halo, CN, NH₂, OH, C₃₋₆cycloalkyl, CF₃, O(C₁₋₆alkyl), or a (CH₂)ᵣ-5-7 membered heteroaryl comprising carbon atoms and 1-4 heteroatoms selected from N, O, and S(O)ₚ;

p is 0, 1, or 2; and r is 0, 1, 2, 3, or 4, wherein additional definitions and specific compounds can be found e.g., in US 2015/0299139, the entire contents of which are incorporated herein by reference.

In a twenty-sixth embodiment, the disclosed Tyk2 inhibitors may be selected from those having the formula:

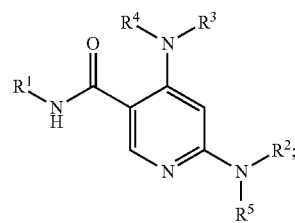

or a pharmaceutically acceptable salt thereof, wherein

R¹ is C₁₋₃alkyl optionally substituted by 0-7 R¹ᵃ

R¹ᵃ at each occurrence is independently hydrogen, deuterium, F, Cl, Br, CF₃ or CN;

R² is C₁₋₆ alkyl substituted with 0-4 R²ᵃ, C₃₋₆ cycloalkyl substituted with 0-4 R²ᵃ, C₆₋₁₀ aryl substituted with 0-4 R²ᵃ, a 5-14 membered heterocycle containing 1-4 heteroatoms selected from N, O, and S, substituted with 0-4 R²ᵃ, NR⁶R⁶ or ORᵇ;

R²ᵃ at each occurrence is independently hydrogen, =O, halo, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ halo alkyl, —(CH₂)ᵣ-3-14 membered carbocycle substituted with 0-1 Rᵃ or a —(CH₂)ᵣ-5-7 membered heterocycle comprising carbon atoms or 1-4 heteroatoms selected from N, O, and S(O)ₚ substituted with 0-2 Rᵃ;

or one R²ᵃ and another R²ᵃ, together with the atoms to which they are attached, combine to form a fused 5-6 membered ring wherein said fused ring may be substituted with 0-2 Rᵃ;

R³ is —(CH₂)ᵣ-3-14 membered carbocycle substituted 0-5 R³ᵃ;

R³ᵃ at each occurrence is independently hydrogen, =O, halo, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ halo alkyl, —(CH₂)ᵣ-3-14 membered carbocycle substituted with 0-3 Rᵃ or a —(CH₂)ᵣ-5-10 membered heterocycle comprising carbon atoms or 1-4 heteroatoms selected from N, O, and S(O)ₚ substituted with 0-3 Rᵃ;

or two R$^{3a}$, together with the atoms to which they are attached, combine to form a fused ring wherein said ring is selected from phenyl and a 5-7 membered heterocycle comprising carbon atoms and 1-4 heteroatoms selected from N, S or O, said fused ring may be further substituted by R$^a$;

R$^4$ and R$^5$ are independently hydrogen, C$_{1-4}$ alkyl substituted with 0-1 R$^f$, (CH$_2$)$_r$-phenyl substituted with 0-3 R$^d$, or a —(CH$_2$)-5-7 membered heterocycle comprising 5 carbon atoms and 1-4 heteroatoms selected from N, O, and S(O)$_p$;

R$^6$ and R$^{11}$ at each occurrence are independently hydrogen, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$, or —(CH$_2$)$_r$-5-7 membered heterocycle comprising carbon atoms and 1-4 heteroatoms selected from N, O, and S(O)$_p$ substituted with 0-3 R$^d$;

R$^a$ at each occurrence is hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^c$, —(CH$_2$)$_r$OC(O)R$^c$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$alkyl substituted with 0-3 R$^f$, C$_{1-6}$haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)p substituted with 0-3 R$^f$;

R$^b$ at each occurrence is hydrogen, C$_{1-6}$ alkyl substituted with 0-3 R$^d$, C$_{1-6}$ halo alkyl, C$_{3-6}$ cycloalkyl substituted with 0-2 R$^d$, or —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ at each occurrence is independently hydrogen, F, Cl, Br, OCF$_3$, CF$_3$, CN, NO$_2$, OR$^e$, —(CH$_2$)$_r$C(O)R$^c$, NR$^e$R$^e$, —NR$^e$C(O)OR$^c$, C$_{1-6}$ alkyl or (CH$_2$)$_r$-phenyl substituted with 0-3 R$^f$;

R$^e$ at each occurrence is independently selected from hydrogen, C$_{1-6}$ alkyl, C$_{3-6}$ cycloalkyl and (CH$_2$)$_r$-phenyl substituted with 0-3 R$^f$;

R$^f$ independently at each occurrence is hydrogen, halo, CN, NH$_2$, OH, C$_{3-6}$ cycloalkyl, CF$_3$, O(C$_{1-6}$alkyl) or a —(CH$_2$)$_r$-5-7 membered heteroaryl comprising carbon atoms and 1-4 heteroatoms selected from N, O, and S(O)$_p$;

p is 0, 1, or 2; and
r is 0, 1, 2, 3, or 4.

In a twenty-seventh embodiment, the disclosed Tyk2 inhibitors may be selected from those having the formula:

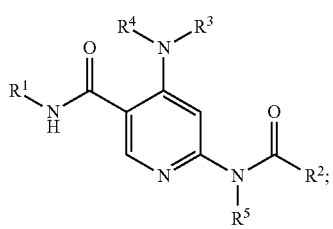

or a pharmaceutically acceptable salt thereof, wherein the variables are as described in WO 2015/069310, the entire contents of which are incorporated herein by reference.

In a twenty-eighth embodiment, the disclosed Tyk2 inhibitors may be selected from those having the formula:

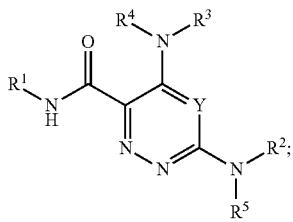

or a pharmaceutically acceptable salt thereof, wherein
Y is N or CR$_6$;
R$^1$ is H, C$_{1-3}$alkyl or C$_{3-6}$cycloalkyl, each optionally substituted by 0-7 R$^{1a}$;
R$^{1a}$ at each occurrence is independently hydrogen, deuterium, F, Cl, Br or CN;
R$^2$ is C$_{1-6}$alkyl, —(CH$_2$)$_r$-3-14 membered carbocycle substituted with 0-1 R$^{2a}$ or a 5-14 membered heterocycle containing 1-4 heteroatoms selected from N, O, and S, each group substituted with 0-4 R$^{2a}$ (for the sake of clarity, R$^2$ is intended to include substituted methyl groups such as —C(O)R$^{2a}$);
R$^{2a}$ at each occurrence is independently hydrogen, =O, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-1 R$^a$ or a —(CH$_2$)$_r$-5-7 membered heterocycle comprising carbon atoms or 1-4 heteroatoms selected from N, O, and S(O)$_p$ substituted with 0-2 R$^a$;
R$^3$ is C$_{3-10}$ cycloalkyl, C$_{6-10}$ aryl or a 5-10 membered heterocycle containing 1-4 heteroatoms selected from N, O, and S, each group substituted with 0-4 R$^{3a}$;
R$^{3a}$ at each occurrence is independently hydrogen, =O, halo, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$ or a —(CH$_2$)$_r$-5-10 membered heterocycle comprising carbon atoms and 1-4 heteroatoms selected from N, O, and S(O)$_p$ substituted with 0-3 R$^a$;

or two R$^{3a}$, together with the atoms to which they are attached, combine to form a fused ring wherein said ring is selected from phenyl and a heterocycle comprising carbon atoms and 1-4 heteroatoms selected from N, O, and S(O)$_p$, each fused ring substituted with 0-3 R$^{a1}$;

R$^4$ and R$^5$ are independently hydrogen, C$_{1-4}$ alkyl substituted with 0-1 R$^f$, (CH$_2$)$_r$-phenyl substituted with 0-3 R$^d$ or a —(CH$_2$)-5-7 membered heterocycle comprising carbon atoms and 1-4 heteroatoms selected from N, O, and S(O)$_p$;

R$^6$ is hydrogen, halo, C$_{1-4}$alkyl, C$_{1-4}$haloalkyl, OC$_{1-4}$alkyl, OC$_{1-4}$haloalkyl, CN, NO$_2$ or OH;

R$^{11}$ at each occurrence is independently hydrogen, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle comprising carbon atoms and 1-4 heteroatoms selected from N, O, and S(O)$_p$ substituted with 0-3 R$^d$;

R$^a$ and R$^{a1}$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)

$NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle comprising carbon atoms and 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ at each occurrence is independently hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl or $(CH_2)_r$-phenyl substituted with 0-3 $R^f$;

$R^e$ at each occurrence is independently selected from hydrogen, $C_{1-6}$ alkyl, $C_{3-6}$ cycloalkyl and $(CH_2)_r$-phenyl substituted with 0-3 $R^f$;

$R^f$ independently at each occurrence is hydrogen, halo, CN, $NH_2$, OH, $C_{3-6}$ cycloalkyl, $CF_3$, $O(C_{1-6}alkyl)$ or a —$(CH_2)_r$-5-7 membered heterocycle comprising carbon atoms and 1-4 heteroatoms selected from N, O, and $S(O)_p$;

p is 0, 1, or 2; and r is 0, 1, 2, 3, or 4, wherein additional definitions and specific compounds are as described in U.S. Pat. No. 9,505,748 and WO 2018/0162889, the entire contents of each of which are incorporated herein by reference.

In a twenty-ninth embodiment, the disclosed Tyk2 inhibitors may be selected from those having the formulae:

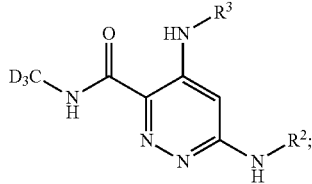

or a pharmaceutically acceptable salt thereof, wherein:
$R^1$ is

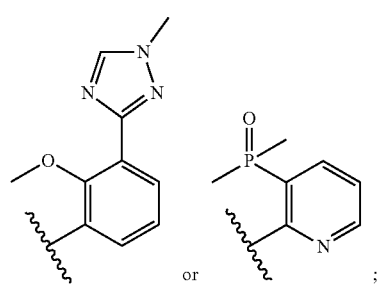

and
$R^2$ is

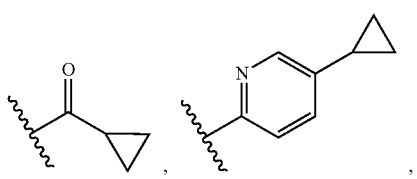

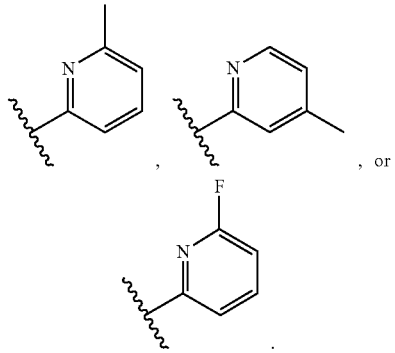

In a thirtieth embodiment, the Tyk2 inhibitor described herein is 6-(cyclopropanecarboxamido)-4-((2-methoxy-3-(1-methyl-1H-1,2,4-triazol-3-yl)phenyl)amino)-N-(methyl-d3)pyridazine-3-carboxamide (BMS-986165), having the following chemical structure:

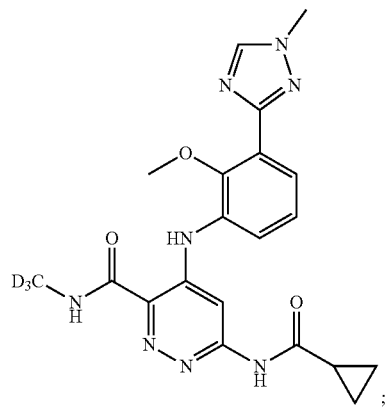 [SMILES: [2H]C([2H])([2H])NC(=O)c1nnc(NC(=O)C2CC2)cc1Nc1cccc(-c2ncn(C)n2)c1OC]

or a pharmaceutically acceptable salt thereof.

The specific dosage and treatment regimen for a disclosed Tyk2 inhibitor to be used in combination with apremilast will depend upon a variety of factors, including age, body weight, general health, sex, diet, time of administration, rate of excretion, drug combination, the judgment of the treating physician, and the severity of the particular disease being treated.

In a thirty-first embodiment, the effective amount of a disclosed Tyk2 inhibitor (e.g., as in any one of the second to thirtieth embodiment) to be used in combination with apremilast ranges from 0.001 to 50 mg/kg body weight/day. For example, as part of a thirty-first embodiment, the effective amount of a disclosed Tyk2 inhibitor (e.g., as in any one of the second to thirtieth embodiment) to be used in combination with apremilast ranges from about 0.1 mg/day to about 250 mg/day, e.g., from about 0.2 mg/day to about 100 mg/day, about 0.5 mg/day to about 50 mg/day, and about 1.0 mg to about 24 mg/day.

In a thirty-second embodiment, the Tyk2 inhibitor described herein is BMS-986165, or a pharmaceutically acceptable salt thereof, and the effective amount of BMS-986165, or a pharmaceutically acceptable salt thereof, ranges from about 0.1 mg/day to about 250 mg/day, about 0.1 mg/day to about 100 mg/day, about 0.1 mg/day to about 50 mg/day, about 0.1 mg/day to about 25 mg/day 0.1 mg/day to about 15 mg/day, about 0.1 mg/day to about 10 mg/day, about 0.5 mg/day to about 15 mg/day, about 0.5 mg/day to about 10 mg/day, about 0.1 mg/day to about 5 mg/day, about 0.5 mg/day to about 5 mg/day, about 1 mg/day to about 25 mg/day, about 2 mg/day to about 14 mg/day, about 2 mg/day to about 12 mg/day, or about 3 mg/day to about 12 mg/day. Alternatively, as part of a thirty-second embodiment, the effective amount of BMS-986165, or a pharmaceutically acceptable salt thereof ranges from about 1 mg/day to about 15 mg/day, about 1 mg/day to about 14 mg/day, about 2 mg/day to about 14 mg/day, about 2 mg/day to about 12 mg/day, or about 3 mg/day to about 12 mg/day.

In a thirty-third embodiment, the Tyk2 inhibitor described herein is BMS-986165, or a pharmaceutically acceptable salt thereof, and the effective amount of BMS-986165, or a pharmaceutically acceptable salt thereof, is about 0.1 mg/day, about 0.5 mg/day, about 1.0 mg/day, about 2 mg/day, about 3 mg/day, about 4 mg/day, about 5 mg/day, about 6 mg/day, about 7 mg/day, about 8 mg/day, about 9 mg/day, about 10 mg/day, about 11 mg/day, or about 12 mg/day. Alternatively, as part of a thirty-third embodiment, the effective amount of BMS-986165, or a pharmaceutically acceptable salt thereof, is about 2 mg/day, about 3 mg/day, about 4 mg/day, about 5 mg/day, about 6 mg/day, about 7 mg/day, about 8 mg/day, about 9 mg/day, about 10 mg/day, about 11 mg/day, or about 12 mg/day. In another alternative, as part of a thirty-third embodiment, the effective concentration of BMS-986165, or a pharmaceutically acceptable salt thereof, is about 1 nM to about 1 µM (e.g., from about 0.01 µM to about 0.1 µM).

3. Apremilast

As described above, apremilast is optically enriched as the (S) enantiomer. In a thirty-fourth embodiment, the stereomeric purity of apremilast in the methods and compositions described herein is greater than 90%, wherein the Tyk2 inhibitor and related features are as described herein e.g., as in any one of the first to thirty-third embodiments. Alternatively, as part of a thirty-fourth embodiment, the stereomeric purity of apremilast in the methods and compositions described herein is greater than 95%, wherein the Tyk2 inhibitor and related features are as described herein e.g., as in any one of the first to thirty-third embodiments. In another alternative, as part of a thirty-fourth embodiment, the stereomeric purity of apremilast in the methods and compositions described herein is greater than 97%, wherein the Tyk2 inhibitor and related features are as described herein e.g., as in any one of the first to thirty-third embodiments. In another alternative, as part of a thirty-fourth embodiment, the stereomeric purity of apremilast in the methods and compositions described herein is greater than 98%, wherein the Tyk2 inhibitor and related features are as described herein e.g., as in any one of the first to thirty-third embodiments. In another alternative, as part of a thirty-fourth embodiment, the stereomeric purity of apremilast in the methods and compositions described herein is greater than 99%, wherein the Tyk2 inhibitor and related features are as described herein e.g., as in any one of the first to thirty-third embodiments. In another alternative, as part of a thirty-fourth embodiment, the stereomeric purity of apremilast in the methods and compositions described herein is greater than 99.5%, wherein the Tyk2 inhibitor and related features are as described herein e.g., as in any one of the first to thirty-third embodiments. In another alternative, as part of a thirty-fourth embodiment, the stereomeric purity of apremilast in the methods and compositions described herein is greater than 99.9%, wherein the Tyk2 inhibitor and related features are as described herein e.g., as in any one of the first to thirty-third embodiments.

Polymorphic forms of apremilast are included in the disclosed methods and compositions and include e.g., those described in U.S. Pat. No. 9,018,243, the entire contents of which are incorporated herein by reference. In a thirty-fifth embodiment, apremilast in the disclosed methods and compositions is a single crystalline form, wherein additional features for apremilast as well as the Tyk2 inhibitor and related features are as described herein e.g., as in any one of the first to thirty-fourth embodiments.

In a thirty-sixth embodiment, apremilast in the disclosed methods and compositions is a single crystalline Form B characterized by X-ray powder diffraction peaks at 2Θ angles selected from 10.1, 13.5°, 20.7°, and 26.9°, wherein additional features for apremilast as well as the Tyk2 inhibitor and related features are as described herein e.g., as in any one of the first to thirty-fourth embodiments. Alternatively, as part of a thirty-sixth embodiment, apremilast in the disclosed methods and compositions is a single crystalline Form B characterized by X-ray powder diffraction peaks at 2Θ angles selected from 10.10, 13.5°, 15.7°, 18.10, 20.7°, 24.7°, and 26.9°, wherein additional features for apremilast as well as the Tyk2 inhibitor and related features are as described herein e.g., as in any one of the first to thirty-fourth embodiments. In another alternative, as part of a thirty-sixth embodiment, apremilast in the disclosed methods and compositions is a single crystalline Form B characterized by X-ray powder diffraction peaks at 2Θ angles selected from 10.10, 13.5°, 15.7°, 16.3°, 18.10, 20.7°, 22.5°, 24.7°, 26.2°, 26.9°, and 29.1, wherein additional features for apremilast as well as the Tyk2 inhibitor and related features are as described herein e.g., as in any one of the first to thirty-fourth embodiments.

In a thirty-seventh embodiment, apremilast in the disclosed methods and compositions is at least 90% single crystalline Form B, wherein additional features for apremilast as well as the Tyk2 inhibitor and related features are as described herein e.g., as in any one of the first to thirty-sixth embodiments. Alternatively, apremilast in the disclosed methods and compositions is at least 95% single crystalline Form B, wherein additional features for apremilast as well as the Tyk2 inhibitor and related features are as described herein e.g., as in any one of the first to thirty-sixth embodiments. In another alternative, apremilast in the disclosed methods and compositions is at least 99% single crystalline Form B, wherein additional features for apremilast as well as the Tyk2 inhibitor and related features are as described herein e.g., as in any one of the first to thirty-sixth embodiments.

The specific dosage and treatment regimen of apremilast, or a pharmaceutically acceptable salt thereof, to be used in combination with a disclosed Tyk2 inhibitor will depend upon a variety of factors, including age, body weight, general health, sex, diet, time of administration, rate of excretion, drug combination, the judgment of the treating physician, and the severity of the particular disease being treated.

For example, in a thirty-eighth embodiment, the effective amount of apremilast, or the pharmaceutically acceptable salt thereof, ranges from about 0.5 mg to about 1000 mg per day, about 1 mg to about 1000 mg per day, about 5 mg to about 500 mg per day, about 10 mg to about 200 mg per day, about 10 mg to about 100 mg per day, about 40 mg to about 100 mg per day, about 20 mg to about 40 mg per day, about 0.1 mg to about 10 mg per day, about 0.5 mg to about 5 mg per day, about 1 mg to about 20 mg per day, and about 1 mg to about 10 mg per day, about 1 mg to about 100 mg per day, about 1 mg to about 80 mg per day, about 5 mg to about 70 mg per day, and about 10 mg to about 60 mg per day, wherein additional features for apremilast as well as the Tyk2 inhibitor and related features are as described herein e.g., as in any one of the first to thirty-seventh embodiments. Alternatively, as part of a thirty-eighth embodiment, the effective amount of apremilast, or the pharmaceutically acceptable salt thereof, ranges from about 10 mg to about 60 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, ranges from about 40 mg to about 100 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, ranges from between about 40 mg to between about 100 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, ranges from about 4 mg to about 10 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, ranges from between about 4 mg to between about 10 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, is about 1 mg per day, about 2 mg per day, about 3 mg per day, about 4 mg per day, about 5 mg per day, about 10 mg per day, about 15 mg per day, about 20 mg per day, about 25 mg per day, about 30 mg per day, about 35 mg per day, about 40 mg per day, about 45 mg per day, about 50 mg per day, about 55 mg per day, or about 60 mg per day, wherein additional features for apremilast as well as the Tyk2 inhibitor and related features are as described herein e.g., as in any one of the first to thirty-seventh embodiments. In another alternative, as part of a thirty-eighth embodiment, the effective amount of apremilast, or the pharmaceutically acceptable salt thereof, is about 30 mg per day or about 60 mg per day, wherein additional features for apremilast as well as the Tyk2 inhibitor and related features are as described herein e.g., as in any one of the first to thirty-seventh embodiments. In another alternative, as part of a thirty-eighth embodiment, apremilast is administered at a dose of about 30 mg once daily, wherein additional features for apremilast as well as the Tyk2 inhibitor and related features are as described herein e.g., as in any one of the first to thirty-seventh embodiments. In another alternative, as part of a thirty-eighth embodiment, apremilast is administered at a dose of about 30 mg twice daily, wherein additional features for apremilast as well as the Tyk2 inhibitor and related features are as described herein e.g., as in any one of the first to thirty-seventh embodiments. In another alternative, as part of a thirty-eighth embodiment, the effective concentration of apremilast is about 100 nM to about 10 µM (e.g., from about 0.1 µM to about 1 µM), wherein additional features for apremilast as well as the Tyk2 inhibitor and related features are as described herein e.g., as in any one of the first to thirty-seventh embodiments.

In a thirty-ninth embodiment, apremilast is titrated to a dosage of about 30 mg administered twice daily using the following titration schedule:

Day 1: about 10 mg in morning;

Day 2: about 10 mg in morning and about 10 mg in evening;

Day 3: about 10 mg in morning and about 20 mg in evening;

Day 4: about 20 mg in morning and about 20 mg in evening;

Day 5: about 20 mg in morning and about 30 mg in evening; and

Day 6 and thereafter: about 30 mg twice daily, wherein additional features for apremilast as well as the Tyk2 inhibitor and related features are as described herein e.g., as in any one of the first to thirty-seventh embodiments. Alternatively, apremilast is titrated to a dosage of between about 40 mg/day to between about 100 mg/day using the following titration schedule:

Day 1: about 10 mg in morning;

Day 2: about 10 mg in morning and about 10 mg in evening;

Day 3: about 10 mg in morning and about 20 mg in evening;

Day 4: about 20 mg in morning and about 20 mg in evening;

Day 5: about 20 mg in morning and about 30 mg in evening; and

Day 6 and thereafter: between about 40 mg/day to between about 100 mg/day, wherein additional features for apremilast as well as the Tyk2 inhibitor and related features are as described herein e.g., as in any one of the first to thirty-seventh embodiments. In another alternative, apremilast is titrated to a dosage of about 20 mg administered twice daily using the following titration schedule:

Day 1: about 10 mg in morning;

Day 2: about 10 mg in morning and about 10 mg in evening;

Day 3: about 10 mg in morning and about 20 mg in evening;

Day 4: about 20 mg in morning and about 20 mg in evening;

Day 5: about 20 mg in morning and about 30 mg in evening; and

Day 6 and thereafter: about 20 mg twice daily, wherein additional features for apremilast as well as the Tyk2 inhibitor and related features are as described herein e.g., as in any one of the first to thirty-seventh embodiments. In yet another alternative, apremilast is titrated to a dosage of between about 4 mg/day to between about 10 mg/day using the following titration schedule:

Day 1: about 1 mg in morning;

Day 2: about 1 mg in morning and about 1 mg in evening;

Day 3: about 1 mg in morning and about 2 mg in evening;

Day 4: about 2 mg in morning and about 2 mg in evening;

Day 5: about 2 mg in morning and about 3 mg in evening; and

Day 6 and thereafter: between about 4 mg/day to between about 10 mg/day, wherein additional features for apremilast as well as the Tyk2 inhibitor and related features are as described herein e.g., as in any one of the first to thirty-seventh embodiments. In yet another alternative, apremilast is titrated to a dosage of about 3 mg administered twice daily using the following titration schedule:

Day 1: about 1 mg in morning;
Day 2: about 1 mg in morning and about 1 mg in evening;
Day 3: about 10 mg in morning and about 2 mg in evening;
Day 4: about 2 mg in morning and about 2 mg in evening;
Day 5: about 2 mg in morning and about 3 mg in evening; and
Day 6 and thereafter: about 3 mg twice daily, wherein additional features for apremilast as well as the Tyk2 inhibitor and related features are as described herein e.g., as in any one of the first to thirty-seventh embodiments.

3. Compositions and Administration

Also provided herein are pharmaceutical compositions comprising a therapeutically effective amount of apremilast, or a pharmaceutically acceptable salt thereof; and a therapeutically effective amount of a Tyk2 inhibitor (e.g., BMS-986165). Features for the disclosed pharmaceutical compositions include elements described above e.g., as in any one of the first to thirty-eighth embodiments.

Further provided are pharmaceutical compositions comprising a therapeutically effective amount of apremilast, or a pharmaceutically acceptable thereof; and a therapeutically effective amount of a Tyk2 inhibitor (e.g., BMS-986165), for use in treating a disease or disorder responsive to the inhibition of PDE4. Features for the disclosed pharmaceutical compositions include elements described above e.g., as in any one of the first to thirty-eighth embodiments.

Pharmaceutical compositions and single unit dosage forms comprising apremilast and a Tyk2 inhibitor (e.g., BMS-986165) alone or together in a fixed dose for administration as described above (e.g., as in any one of the first to thirty-eighth embodiments) is included. Single unit dosage forms of the disclosed methods and compositions are suitable for oral, mucosal (e.g., nasal, sublingual, vaginal, buccal, or rectal), parenteral (e.g., Subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suit able for parenteral administration to a patient; and sterile solids (e.g., crystalline or amorphous solids) that can be reconstituted to provide liquid dosage forms suitable for parenteral administration to a patient.

The composition, shape, and type of dosage forms of the will typically vary depending on their use. For example, a dosage form used in the acute treatment of inflammation or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

In a thirty-ninth embodiment, apremilast in the disclosed methods and compositions is administered parenterally, transdermally, mucosally, nasally, buccally, sublingually, or orally, wherein additional features for apremilast as well as the Tyk2 inhibitor and related features are as described herein e.g., as in any one of the first to thirty-eighth embodiments. Alternatively, as part of a thirty-ninth embodiment, apremilast in the disclosed methods and compositions is administered orally, wherein additional features for apremilast as well as the Tyk2 inhibitor and related features are as described herein e.g., as in any one of the first to thirty-eighth embodiments.

In a fortieth embodiment, apremilast in the disclosed methods and compositions is administered orally in the form of a tablet or a capsule, wherein additional features for apremilast as well as the Tyk2 inhibitor and related features are as described herein e.g., as in any one of the first to thirty-ninth embodiments.

In a forty-first embodiment, apremilast in the disclosed methods and compositions is formulated as an extended release form, wherein additional features for apremilast as well as the Tyk2 inhibitor and related features are as described herein e.g., as in any one of the first to thirty-ninth embodiments.

In a forty-second embodiment, apremilast in the disclosed methods and compositions is formulated as an immediate release form, wherein additional features for apremilast as well as the Tyk2 inhibitor and related features are as described herein e.g., as in any one of the first to thirty-ninth embodiments.

In a forty-third embodiment, both the apremilast and the Tyk2 inhibitor in the disclosed methods and compositions are administered in fixed dosage combination as a once a day formulation, wherein additional features for apremilast as well as the Tyk2 inhibitor and related features are as described herein e.g., as in any one of the first to forty-second embodiments.

4. Conditions Treated by the Methods and Compositions Disclosed Herein

Diseases or disorders that are responsive to the inhibition of PDE4 using the methods and compositions disclosed herein include e.g., viral, genetic, inflammatory, allergic, and autoimmune conditions.

In one aspect, the disease or disorder responsive to the inhibition of PDE4 is selected from chronic obstructive pulmonary disease, asthma, chronic pulmonary inflammatory disease, hyperoxic alveolar injury, inflammatory skin disease, psoriasis, psoriatic arthritis, rheumatoid arthritis, rheumatoid spondylitis, osteoarthritis, atopic dermatitis, rheumatoid spondylitis, depression, osteoarthritis, contact dermatitis, ankylosing spondylitis, lupus, lupus nephritis, cutaneous lupus erythematosus, systemic lupus erythrematosus, erythema nodosum leprosum, Sjagren's syndrome, inflammatory bowel disease, Crohn's Disease, Behget's Disease, and ulcerative colitis.

In one aspect, the disease or disorder responsive to the inhibition of PDE4 is selected from psoriasis, psoriatic arthritis, contact dermatitis, systemic lupus erythrematosus, cutaneous lupus erythematosus, and ulcerative colitis.

In one aspect, the disease or disorder responsive to the inhibition of PDE4 is psoriasis. In another aspect, the disease or disorder responsive to the inhibition of PDE4 is psoriasis and the subject being treated is a candidate for phototherapy or systematic therapy.

In one aspect, the disease or disorder responsive to the inhibition of PDE4 is plaque psoriasis. In another aspect, the disease or disorder responsive to the inhibition of PDE4 is plaque psoriasis and the subject being treated is a candidate for phototherapy or systematic therapy.

In one aspect, the disease or disorder responsive to the inhibition of PDE4 is moderate to severe plaque psoriasis. In another aspect, the disease or disorder responsive to the inhibition of PDE4 is severe plaque psoriasis and the subject being treated is a candidate for phototherapy or systematic therapy.

In one aspect, the disease or disorder responsive to the inhibition of PDE4 is psoriatic arthritis.

In one aspect, the disease or disorder responsive to the inhibition of PDE4 is active psoriatic arthritis.

In one aspect, the disease or disorder responsive to the inhibition of PDE4 is heart disease, such as congestive heart failure, cardiomyopathy, pulmonary edema, endotoxin-mediated septic shock, acute viral myocarditis, cardiac allograft rejection, and myocardial infarction.

In one aspect, the disease or disorder responsive to the inhibition of PDE4 is HIV, hepatitis, adult respiratory distress syndrome, bone-resorption diseases, cystic fibrosis, septic shock, sepsis, endotoxic shock, hemodynamic shock, sepsis syndrome, post ischemic reperfusion injury, meningitis, fibrotic disease, cachexia, graft rejection, osteoporosis, multiple sclerosis, and radiation damage.

In one aspect, the disease or disorder responsive to the inhibition of PDE4 is cancer of the head, thyroid, neck, eye, skin, mouth, throat, esophagus, cheat, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof.

In one aspect, the disease or disorder responsive to the inhibition of PDE4 is multiple myeloma, malignant melanoma, malignant glioma, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, multiple myeloma and acute, lymphoblastic leukemia, myelogenous leukemia, lymphocytic leukemia, and myelocytic leukemia.

In one aspect, the disease or disorder responsive to the inhibition of PDE4 is a solid tumor, such as sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, syn-ovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma.

EXEMPLIFICATION

1. Materials

TABLE 1

Whole blood assay: Study Materials and Reagents.

| Name of Material | Vendor | Catalog#/Lot# |
| --- | --- | --- |
| Null TruCulture ® Tube | Myriad RBM | 782-001086/11437EO |
| CD3/CD28 TruCulture ® Tube | Myriad RBM | 782-001125/11761EQ |
| IL-1β, IL-6 and IL-23 recombinant proteins | R&D Systems | 201-LB/206-IL/1290-IL |
| Magpix Kit with Th17 Cytokines | Millipore | HT17MG-14K-PX25 |
| Abcam Simplestep IL-22 ELISA kit | Abcam | ab216170 |

TABLE 2

LPS stimulated PBMCs assay: Study Materials and Reagents

| Name of Material | Vendor | Catalog# |
| --- | --- | --- |
| SepMate ® PBMC Isolation Tube | Stemcell | 85450 |
| Ficoll-Paque PLUS | GE Healthcare | 17-1440-03 |
| RPMI Medium 1640 | Gibco | 11875 |
| Fetal bovine serum (FBS) | Gibco | 10082-147 |
| PBS | Gibco | 10010-023 |
| 40 µm cell strainer | Falcon | 352340 |
| RBC lysis buffer | eBioscience | 00-4333-57 |
| 96 well plates | Corning Costar | 3610 |
| 96 well plates for supernatants | Corning Costar | 3363 |
| Lipopolysaccharides (LPS) | Sigma | L4391 |
| Bio-Plex Pro ™ Human Th17 Cytokine IL-23 Set | Bio-Rad | 171BA009M |
| Bio-Plex Pro ™ Human Inflammation Panel 1 IL-12 (p40) Set | Bio-Rad | 171BL015M |
| Bio-Plex Pro ™ Human Cytokine 27-plex Assay | Bio-Rad | M500KCAF0Y |

TABLE 3

Test Articles for Studies

| Compound | Lot# | Company |
| --- | --- | --- |
| Apremilast PDE4i | 61983-04 | Celgene Corporation |
| BMS- 986165 | Available from Medkoo (555349) or MedChemExpress (HY-117287) | Celgene Corporation |

2. General Methods

Whole blood was received through the Celgene Donor program after informed consent and donor deidentification. All volunteers were healthy and were not on any medications for at least 72 hours prior to the blood draw. Blood was collected in sodium heparin tubes. The assay was started within 2 hours of the blood draw.

An ex-vivo stimulation of healthy donor human whole blood was performed under two different stimulation conditions. Condition Th0 was a stimulation with TruCulture® tubes containing anti-CD3/anti-CD28. Condition Th17 was a stimulation with TruCulture® tubes containing anti-CD3/anti-CD28 plus IL-1β, IL-6 and IL-23. Whole blood was separated into 15 milliliter conical tubes and pre-treated with DMSO, apremilast alone, BMS-986165 alone or BMS-986165 combined with apremilast. Final concentrations were 0.2% DMSO, 1 μM for apremilast alone, 1 μM, 0.1 μM, 0.01 μM and 0.001 μM BMS-986165 alone and in combination with 1 μM apremilast. Blood was mixed well and then incubated in a 37° C./5% $CO_2$ incubator for 1 hour.

The anti-CD3/anti-CD28 (200 ng/ml and 330 ng/ml final concentrations respectively) TruCulture® tubes were thawed on the bench top for 30 minutes and then labeled. Plungers were pressed and then broken off. TruCulture® tubes were placed in a rack standing upright such that the plunger side is pointing down in the rack and the tube-cap is pointing up. While blood was incubating with compound Human recombinant IL-6, IL-1β and IL-23 were added to all Th17 tubes in the following concentrations: 120 ng IL-6, 120 ng IL-1b and 150 ng IL-23. One ml of the pre-treated whole blood was placed in each tube, using sterile pyrogen-free pipette tips. The cap was replaced and the contents of the tube were mixed by inverting 3 times. The tubes were immediately placed in a 37° C. heat block and incubated for 42 hours (tube-cap end). After the 42 hours the tubes were removed from the heat block, tops were unscrewed and 250 μl of the supernatant was removed and transferred into three 96-well polypropylene plates. Samples were immediately frozen at −80° C. The supernatants were then thawed at room temperature and tested neat for cytokine production by Luminex Multi-Plex MagPix technology (Millipore) or IL-22 by ELISA (Abcam). The manufacturer's procedures were followed accordingly.

Peripheral blood mononuclear cells (PBMCs) isolation: Whole blood was received through the Celgene Donor program after informed consent and donor deidentification. All volunteers were healthy and were not on any medications for at least 72 hours prior to the blood draw. Blood was collected in Sodium Heparin tubes and were used within 2 hours of the blood draw for PBMCs isolation. Before PBMCs isolation, whole blood was diluted 1:1 with PBS solution containing 2% FBS (2% FBS-PBS). 13 ml of Ficoll-Paque solution was loaded in the SepMate® tube and 25 ml of diluted blood was loaded on top of the Ficoll-Paque. Centrifugation at 1200 g for 15 minutes with the brake on for cell separation, after which isolated PBMCs were transferred into a new tube. PBMCs were washed with 2% FBS-PBS and centrifuged at 800 g 10 minutes. Pellets were resuspended in 2% FBS-PBS and filtered through a 40 μm cell strainer to obtain single-cell suspension. 3 ml of RBC lysis buffer were used to eliminate red blood cells in the isolated population. Isolated PBMCs were washed with 2% FBS-PBS and were resuspended in RPMI growth medium containing 10% FBS and antibiotics.

For Example 6-11, PBMCs from 9 healthy donors were isolated and LPS-stimulated ex-vivo for IL-23, IL-12p40, IL-12p70, TNF-α, IFN-γ and MCP-1 cytokine analysis. PBMCs were plated in 96 well plate at a density of 200,000 cells per well in 200 of RPMI growth medium containing 10% FBS followed by treatment with DMSO and compounds. Each well received the same amount of DMSO, which is 0.3% v/v as final concentration. Series dilutions of compound treatment was performed according to Table 4 shown below. After two hours of compound treatment, LPS 100 ng/ml as final concentration was used as the stimulator. PBMCs were then incubated in a 37° C./5% $CO_2$ incubator for 16 hours.

TABLE 4

Compound treatment conditions for PBMC assays

| Treatment | Stimulation |
|---|---|
| DMSO | No |
| DMSO | LPS 100 ng/ml |
| Single compound: | LPS 100 ng/ml |
| Tyk2i (BMS-986165): 2 μM max, 8 point, 3 fold dilution series (Final concentration were 2 μM, 0.66 μM, 0.22 μM, 0.07 μM, 0.02 μM, 0.008 μM, 0.002 μM, 0.0009 μM) | |
| Single compound: Apremilast (CC-10004): 3 μM max, 8 point, 3 fold dilution series (Final concentration were 3 μM, 1 μM, 0.33 μM, 0.11 μM, 0.037 μM, 0.012 μM, 0.004 μM, 0.001 μM) | LPS 100 ng/ml |
| Combination of Tyk2i and Apremilast: Tyk2i (BMS-986165): 2 μM max, 8 point, 3 fold dilution series Apremilast CC-10004: fixed concentration at 1 μM | LPS 100 ng/ml |
| Combination of Tyk2i and Apremilast: Tyk2i (BMS-986165): 2 μM max, 8 point, 3 fold dilution series Apremilast CC-10004: fixed concentration at 0.3 μM | LPS 100 ng/ml |
| Combination of Tyk2i and Apremilast: Tyk2i (BMS-986165): 2 μM max, 8 point, 3 fold dilution series Apremilast CC-10004: fixed concentration at 0.1 μM | LPS 100 ng/ml |
| Combination of Tyk2i and Apremilast: Tyk2i (BMS-986165): 2 μM max, 8 point, 3 fold dilution series Apremilast CC-10004: fixed concentration at 0.037 μM | LPS 100 ng/ml |

After 16 hours incubation, supernatants were collected into new 96-well polypropylene plates and centrifuged at 4000 rpm for 10 minutes to get rid of cell debris. Cytokine production was measured by Luminex Bio-Plex Multiplex Immunoassay (Bio-Rad) according to the manufacturer's procedures. To ensure that supernatant level was within the range of the standard cytokine for the assay, samples were diluted 5 fold for IL-12p40 and 27-plex assays, and used neat for IL-23 assay.

3. Data Analysis

Data processing for the cytokine analysis was done using Milliplex Analyst (Millipore), and raw data was exported to Excel template for the cytokine analysis. Data from the template was plotted using GraphPad Prism 7.0 (GraphPad Software, Inc., La Jolla, Calif.) and expressed as pg/ml or % of control. Statistical analysis was also performed using One Way Anova and Dunnett's Post Test.

Data processing for PBMCs assays was done using Bio-plex manager, and raw data was exported to Excel template for the cytokine analysis. Data was plotted using GraphPad Prism 7.0 (GraphPad Software, Inc., La Jolla, Calif.) and expressed as % of DMSO control. Statistical analysis was performed using One Way ANOVA and Tukey's multiple comparisons test.

To evaluate the combinatory effect of apremilast and BMS-986165, data from the two independent treatments were analyzed by comparing the combinatory response against the theoretical additive response of the two agents. The expected additive effect of two agents (A and B) was calculated using the fractional product method: (fu)A,B= (fu)A×(fu)B; where fu=fraction unaffected by treatment. A synergism of a combination is determined when the observed fraction unaffected in combination is less than (fu)A,B, whereas an additive effect is determined when the observed fraction unaffected in combination equals (fu)A,B. A partially additive effect is indicated when the observed fraction unaffected in combination is greater than (fu)A,B.

Example 1

Figure 1:
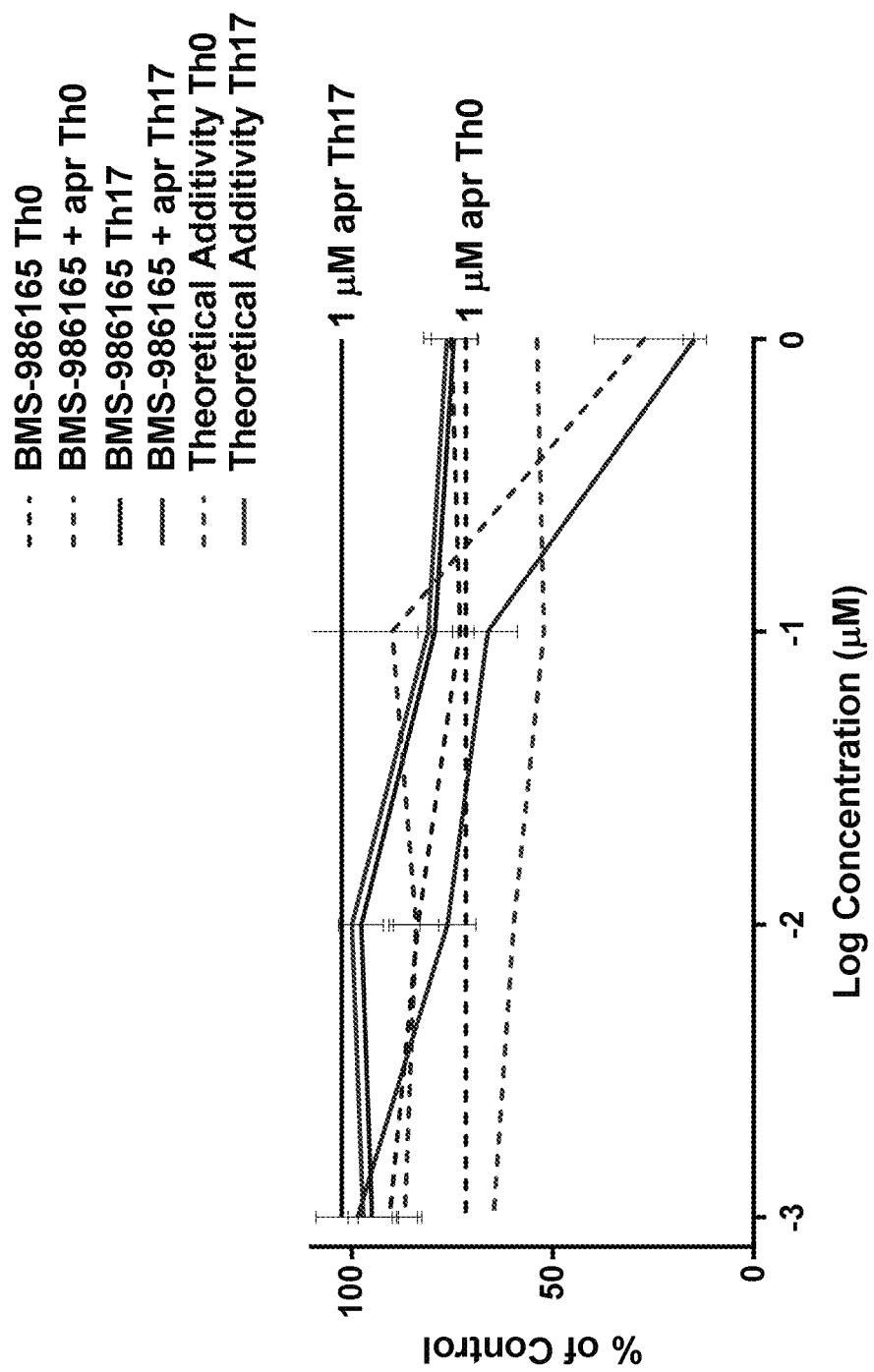
FIG. 1 illustrates interleukin-17a (IL-17a) cytokine production (percent of control) by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.
Figure 2:
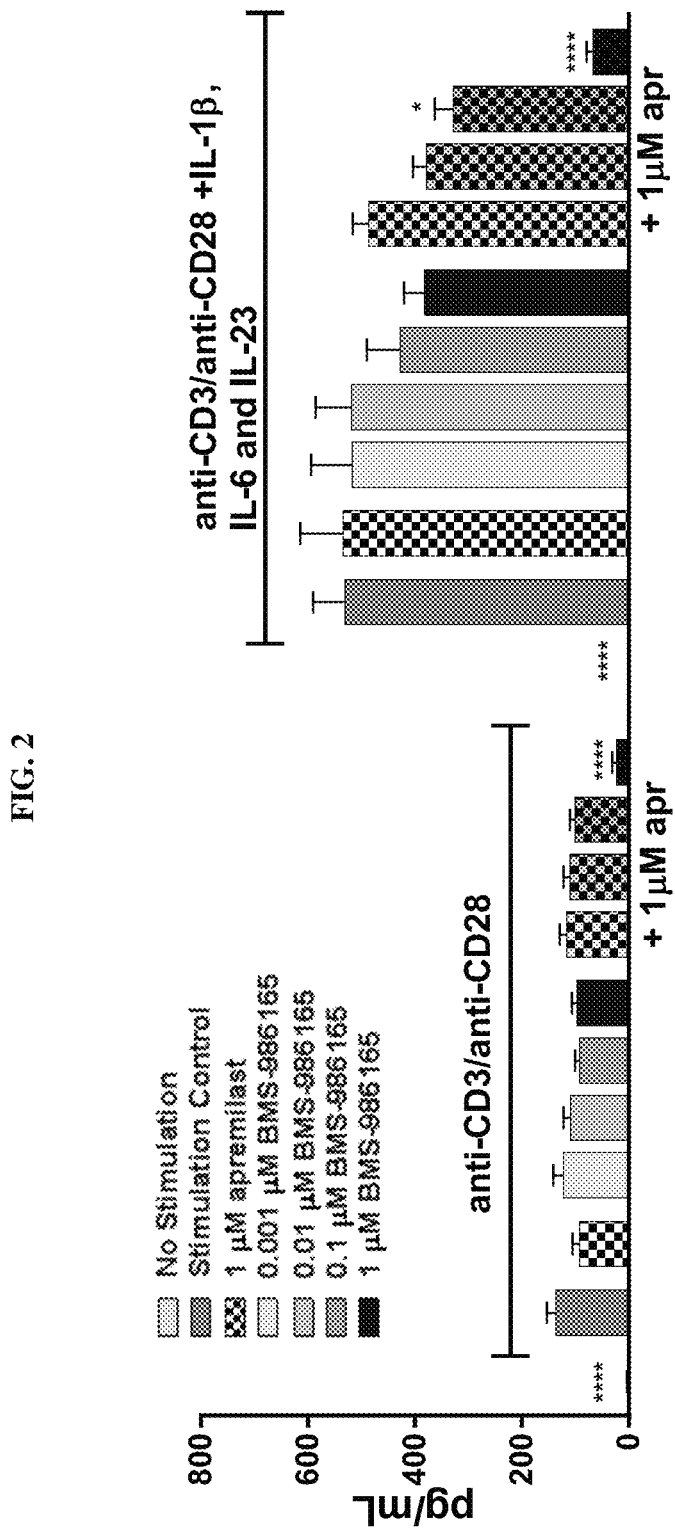
FIG. 2 illustrates interleukin-17A (IL-17A) cytokine production by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.

Interleukin 17A Cytokine Production by Apremilast and BMS-986165 in Anti-CD3/Anti-CD28 (Th0) or Anti-CD3/Anti-CD28, IL-1β, IL-6 and IL-23 (Th17) Stimulated Whole Blood Whole blood from 4 healthy donors were analyzed for IL-17A, IL-17F, IL-22, TNF-α and GM-CSF cytokine production in both Th0 and Th17 conditions. The blood was pre-treated with apremilast and Tyk2 inhibitor BMS-986165 both alone and in combination using the TruCulture® Tube System. The IL-17A results located in FIG. 1 show the IL-17A % of control and all data is normalized to the Th17 DMSO control. Apremilast inhibited 28% of IL-17A cytokine expression under Th0 conditions and had no effect in Th17 conditions. BMS-986165 had a similar effect under both stimulation conditions and inhibited 10-25% of IL-17A expression at 0.001-1 µM. When apremilast was combined with BMS-986165 under Th0 conditions there was synergy seen with 1 µM BMS-986165 with a 65% reduction in IL-17A. Under Th17 conditions there was synergy with the combination of 1 µM apremilast and 0.01 µM, 0.1 µM and 1 µM BMS-986165 with inhibition of 24%, 44% and 85% of IL-17A respectively. FIG. 2 shows the picograms per milliliter levels of IL-17A. Levels of IL-17A increased in the Th17 stimulation conditions by 387% compared to the Th0 stimulation. In Th0 conditions apremilast reduced IL-17A levels from 138 pg/mL to 93 pg/mL. BMS-986165, at 1 µM reduced IL-17A levels to 97 pg/mL. The combination of apremilast with 1 µM BMS-986165 further reduced IL-17A levels to 24 pg/mL with the Th0 stimulation. Under Th17 conditions the stimulation control measured 532 pg/mL and apremilast did not inhibit IL-17A levels. BMS-986165 reduced IL-17A levels to 519 pg/mL at 0.01 µM, 428 pg/mL at 0.1 µM and 383 pg/mL at 1 µM. The combination of 1 µM apremilast with BMS-986165 reduced IL-17A levels to 379 pg/mL at 0.01 µM, 328 pg/mL at 0.1 µM and 68 pg/mL at 1 µM BMS-986165.

Example 2

Figure 3:
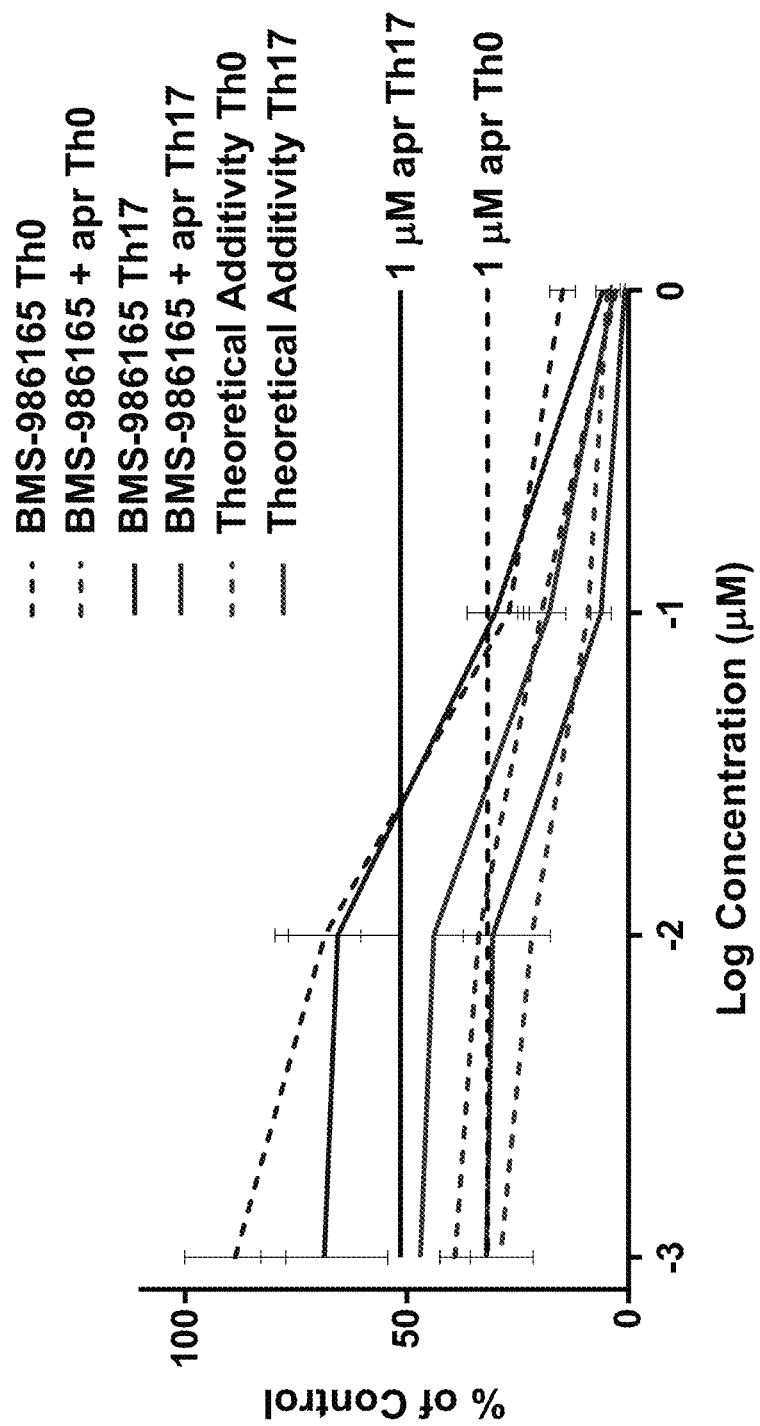
FIG. 3 illustrates interleukin-17F (IL-17F) cytokine production (percent of control) by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.
Figure 4:
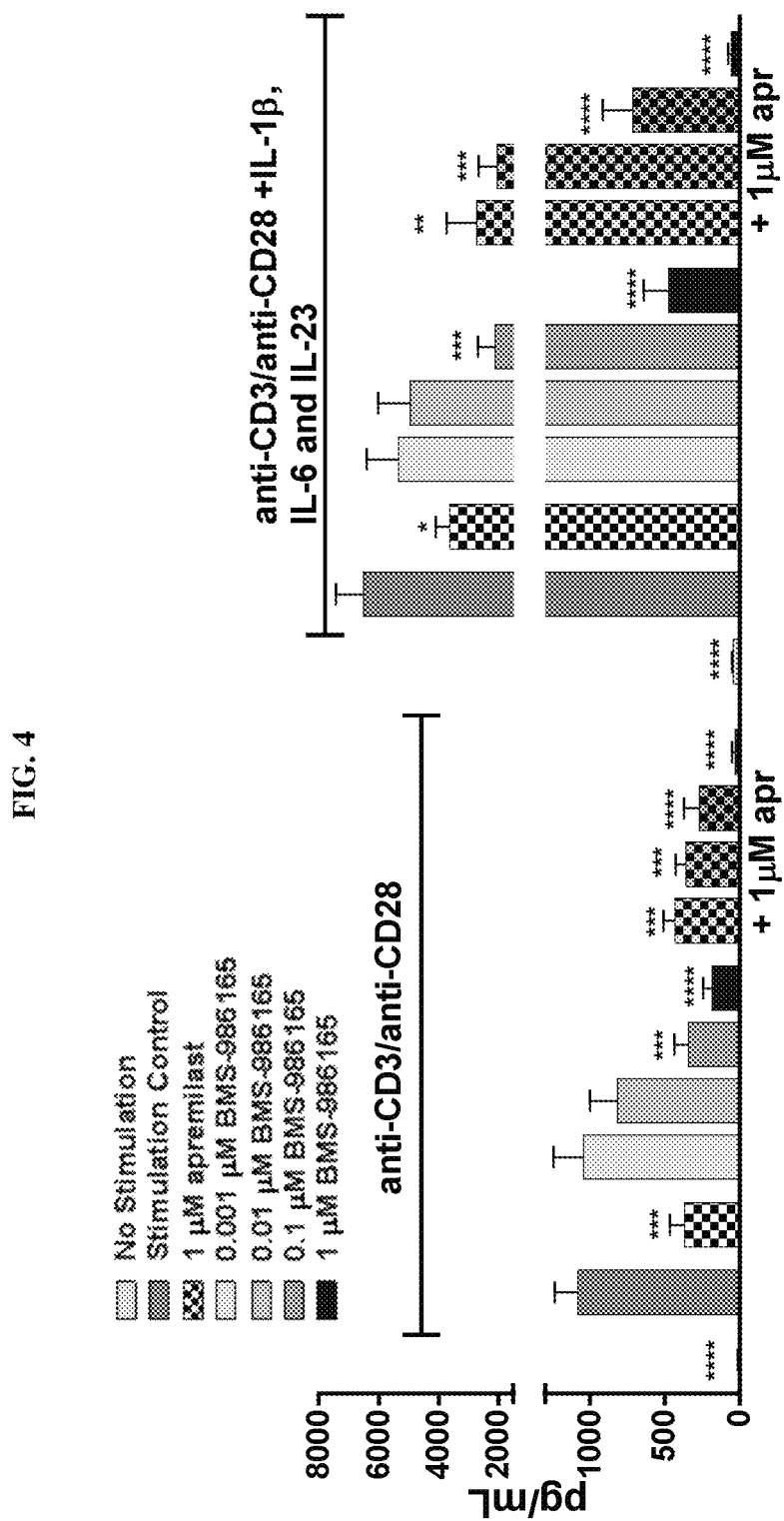
FIG. 4 illustrates interleukin-17F (IL-17F) cytokine production by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.

Interleukin 17F Cytokine Production by Apremilast and BMS-986165 in Anti-CD3/Anti-CD28 (Th0) or Anti-CD3/Anti-CD28, IL-1β, IL-6 and IL-23 (Th17) Stimulated Whole Blood IL-17F cytokine expression data is in FIG. 3 and FIG. 4. Apremilast inhibited 69% of IL-17F production under Th0 conditions and 49% under Th17 conditions. BMS-986165 had a similar effect on IL-17F with both the Th0 and Th17 stimulation. There was 31% inhibition at the lowest concentration of 0.001 µM and a dose response with 34% inhibition at 0.01 µM, 70% inhibition at 0.1 µM and 95% inhibition of IL-17F expression at 1 µM (Th17 results). The combination of 1 µM apremilast with BMS-986165 under Th0 conditions was partially additive with inhibition ranging from 60% at 0.001 to 95% at 1 µM. Under Th17 conditions lower concentrations of BMS-986165 combined with apremilast showed synergy. Apremilast combined with BMS-986165 at 0.001 µM inhibited 68% of IL-17F, 0.01 µM inhibited 70%, 0.1 µM inhibited 94% and 1 µM inhibited 99% of IL-17F production under Th17 stimulation conditions. Levels of IL-17F in the Th0 stimulation control were 1085 pg/mL and increased to 6524 pg/mL in the Th17 stimulation. Apremilast reduced IL-17F to 368 pg/mL in the Th0 stimulation and to 3643 pg/mL in the Th17 stimulation. BMS-986165 significantly reduced IL-17F at 0.1 and 1 µM in both stimulation conditions. There was significant inhibition of IL-17F at all concentrations of BMS-986165 when combined with apremilast and under both stimulation conditions.

Example 3

Figure 5:
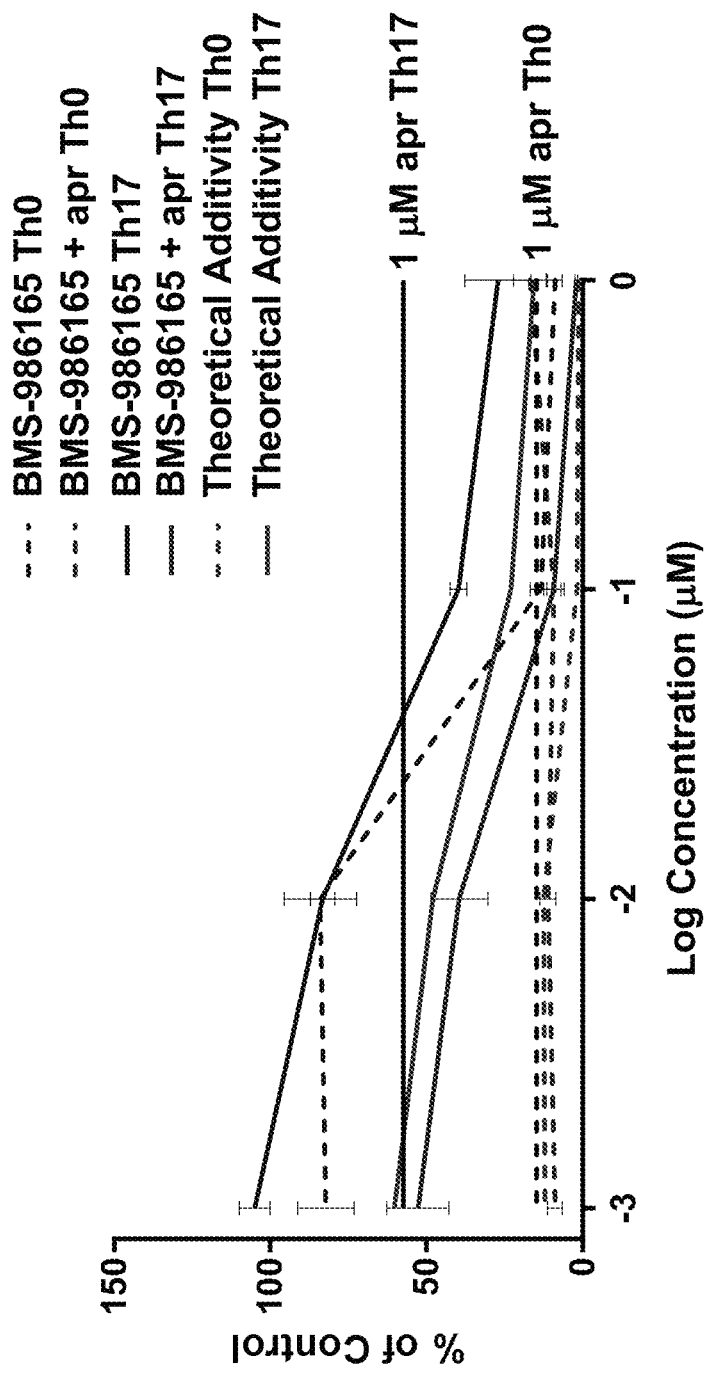
FIG. 5 illustrates interleukin-22 (IL-22) cytokine production (percent of control) by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.
Figure 6:
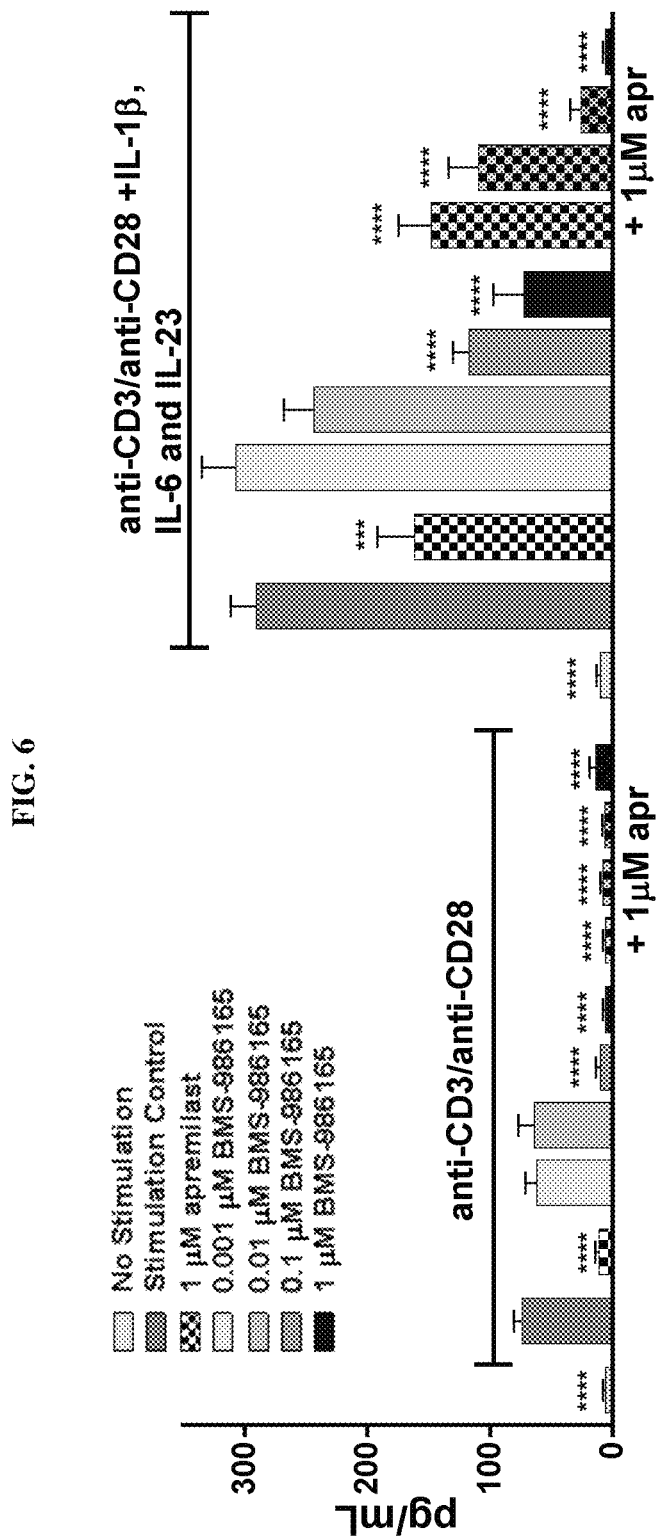
FIG. 6 illustrates interleukin-22 (IL-22) cytokine production by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.

Interleukin 22 Cytokine Production by Apremilast and BMS-986165 in Anti-CD3/Anti-CD28 (Th0) or Anti-CD3/Anti-CD28, IL-1β, IL-6 and IL-23 (Th17) Stimulated Whole Blood IL-22 cytokine expression data is in FIG. 5 and FIG. 6. Apremilast inhibited 85% of IL-22 cytokine expression under Th0 conditions and 41% under Th17 conditions. Under Th0 stimulation condition BMS-986165 inhibited 16% of IL-22 at 0.01 µM, 86% at 0.1 µM and 91% at 1 µM. Under Th17 stimulation conditions BMS-986165 had no effect on IL-22 cytokine expression at 0.001 µM but inhibited 17% at 0.01 µM, 60% at 0.1 µM and 70% at 1 µM. Under Th0 conditions the combination had similar effects to apremilast alone with 90% inhibition at all concentrations of BMS-986165. The combination under Th17 conditions was synergist at 0.01 µM with 60% inhibition and at 0.1 µM with 90% inhibition of IL-22 cytokine expression. The Th0 stimulation control had 1085 pg/mL of IL-22 and the Th17 control was 6524 pg/mL. Apremilast significantly lowered IL-22 levels to 368 pg/mL in the Th0 conditions and 3643 pg/mL in the Th17 conditions. BMS-986165 significantly lowered IL-22 cytokine expression in both stimulation conditions at 0.1 µM and 1 µM. There was significant inhibition of IL-22 at all concentrations of BMS-986165 when combined with apremilast and under both stimulation conditions.

Example 4

Figure 7:
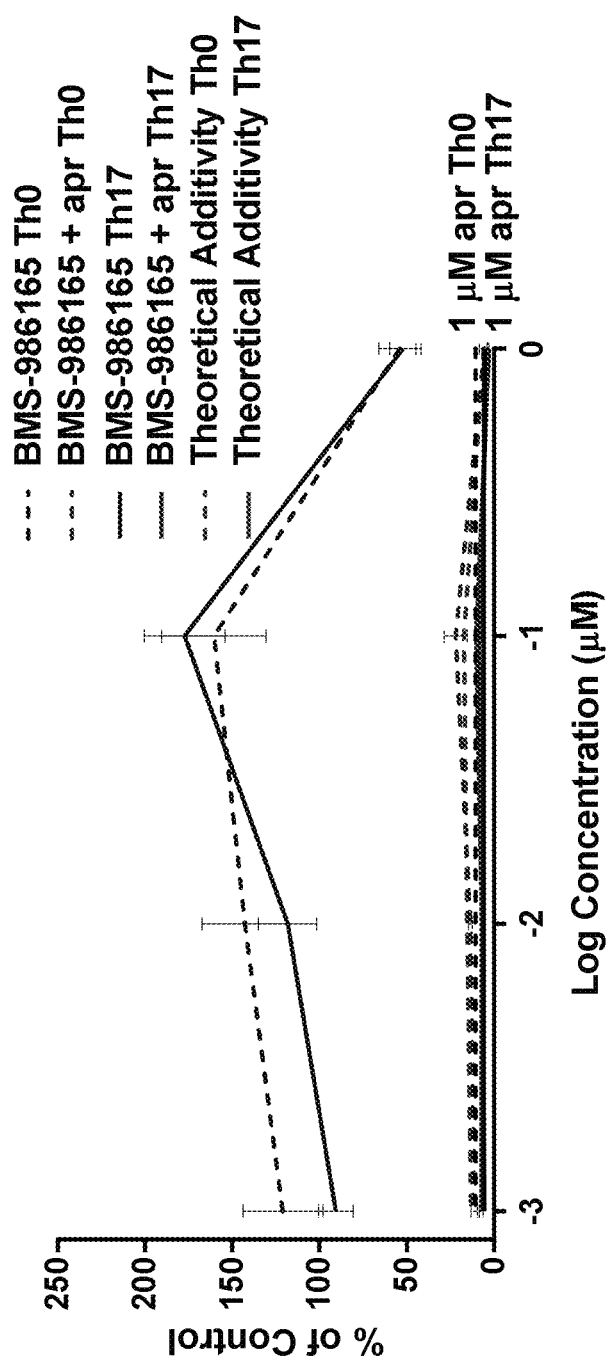
FIG. 7 illustrates tumor necrosis factor alpha (TNF-α) cytokine production (percent of control) by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.
Figure 8:
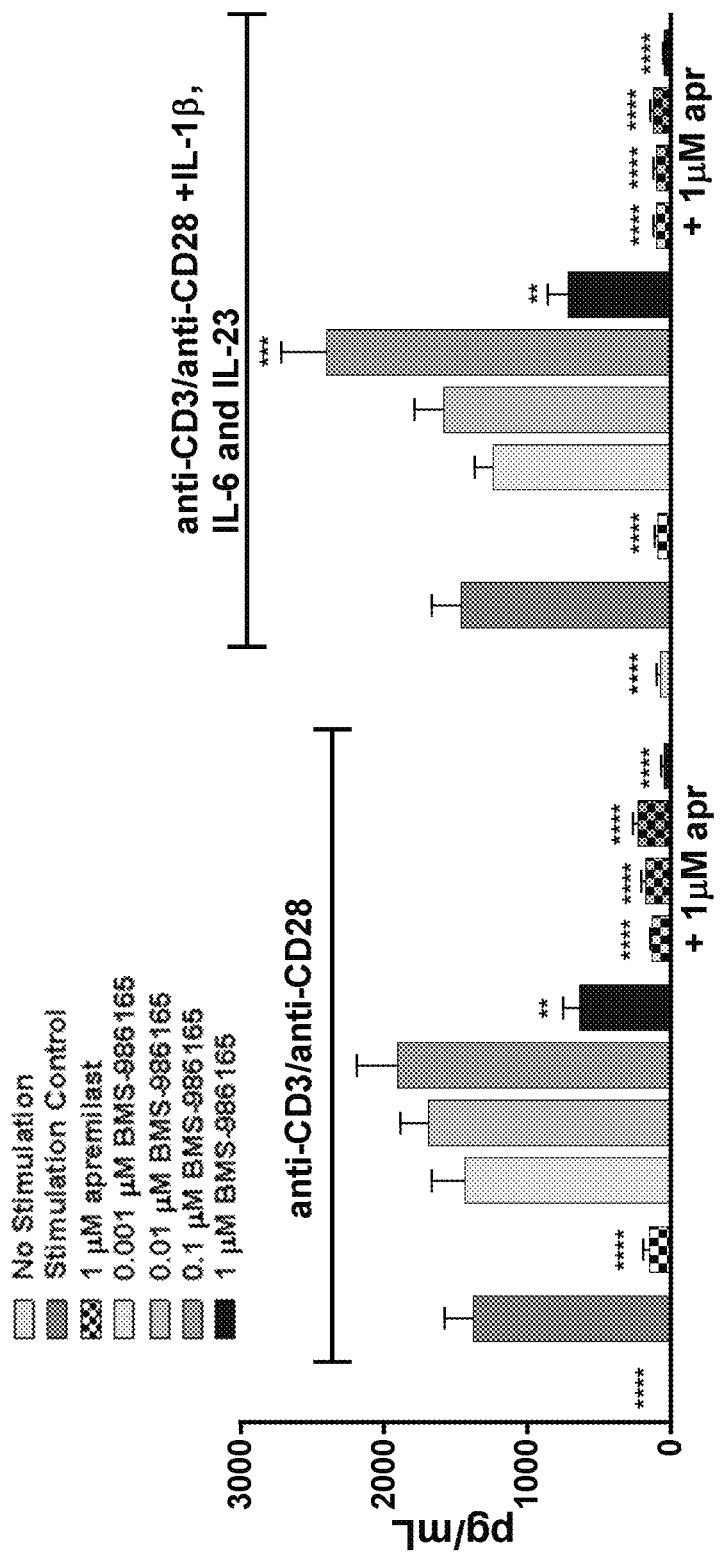
FIG. 8 illustrates tumor necrosis factor alpha (TNF-α) cytokine production by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.

TNF-α Cytokine Production by Apremilast and BMS-986165 in Anti-CD3/Anti-CD28 (Th0) or Anti-CD3/Anti-CD28, IL-1β, IL-6 and IL-23 (Th17) Stimulated Whole Blood TNF-α cytokine expression data is located in FIG. 7 and FIG. 8. Apremilast inhibited 90% of TNF-α levels in Th0 conditions and 94% in Th17 conditions. In the Th0 stimulation BMS-986165 increased TNF-α expression by 21% at 0.001 µM, 43% at 0.01 µM and 61% at 0.1 µM. At the highest concentration of 1 µM BMS-986165 inhibited 66% of TNF-α cytokine expression. There was a similar increase in TNF-α production seen with BMS-986165 under Th17 conditions with a 19% increase at 0.01 µM and a 77% increase at 0.1 µM. There was also inhibition of TNF-α (68%) with 1 µM BMS-986165 under Th17 stimulation conditions. The combination of 1 µM apremilast with BMS-986165 reduced levels of TNF-α by 80-95% (Th0) and 93-96% (Th17), a similar effect to single agent apremilast. Both stimulation conditions had a similar effect on levels of TNF-α with the Th0 stimulation control of 1380 pg/mL and the Th17 stimulation control of 1436 pg/mL. Apremilast significantly inhibited TNF-α by reducing levels to 148 pg/mL in Th0 conditions and 91 pg/mL in Th17 conditions. The increase in TNF-α levels by BMS-986165 was significant in Th17 conditions at 0.1 µM. The inhibition of TNF-α levels with 1 µM BMS-986165 was significant under both stimulation conditions. The combination of apremilast with BMS-986165 significantly inhibited TNF-α levels with all concentrations and in both stimulation conditions.

Example 5

Figure 9:
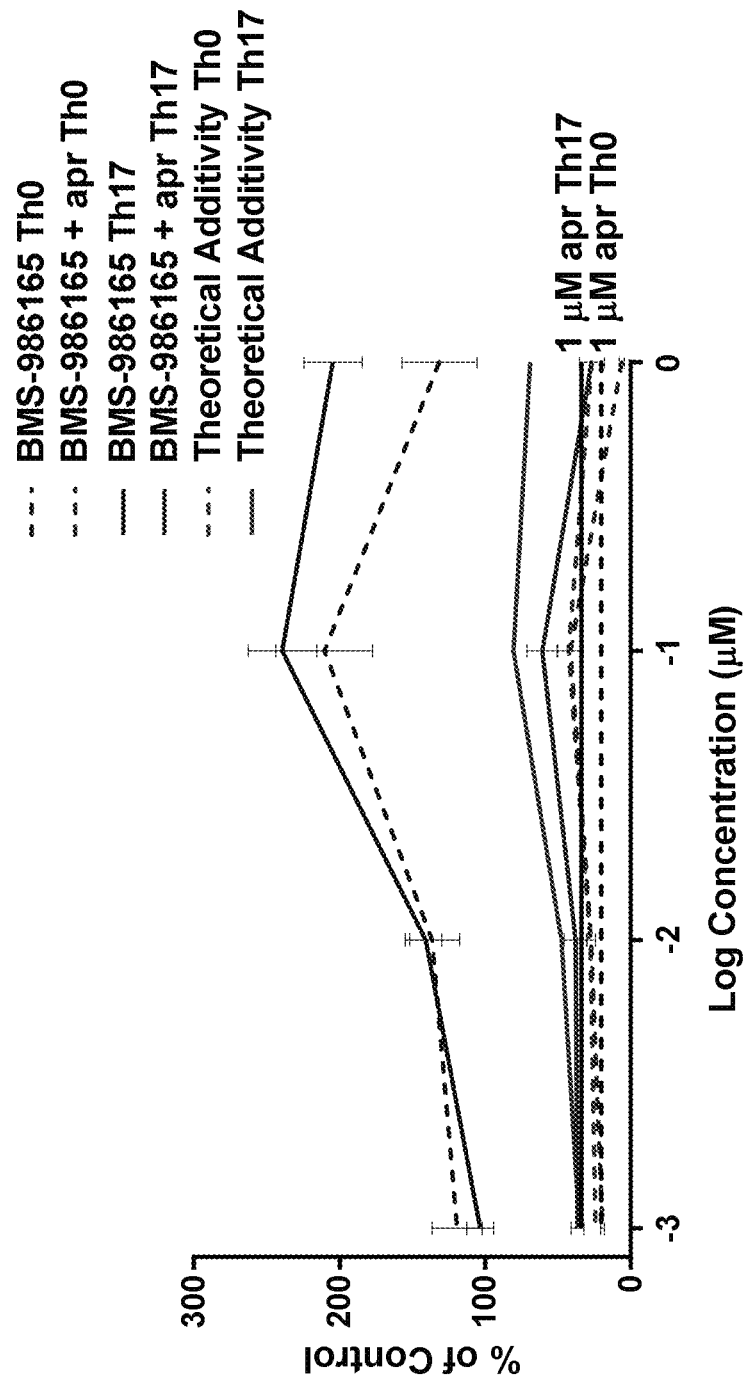
FIG. 9 illustrates granulocyte-macrophage colony-stimulating factor (GM-CSF) cytokine production (percent of control) by apremilast and BMS-986165 in anti-CD3/anti-CD28 (Th0) or anti-CD3/anti-CD28, IL-1β, IL-6 and IL-23 (Th17) stimulated whole blood—TruCulture® tube assay.
Figure 10:
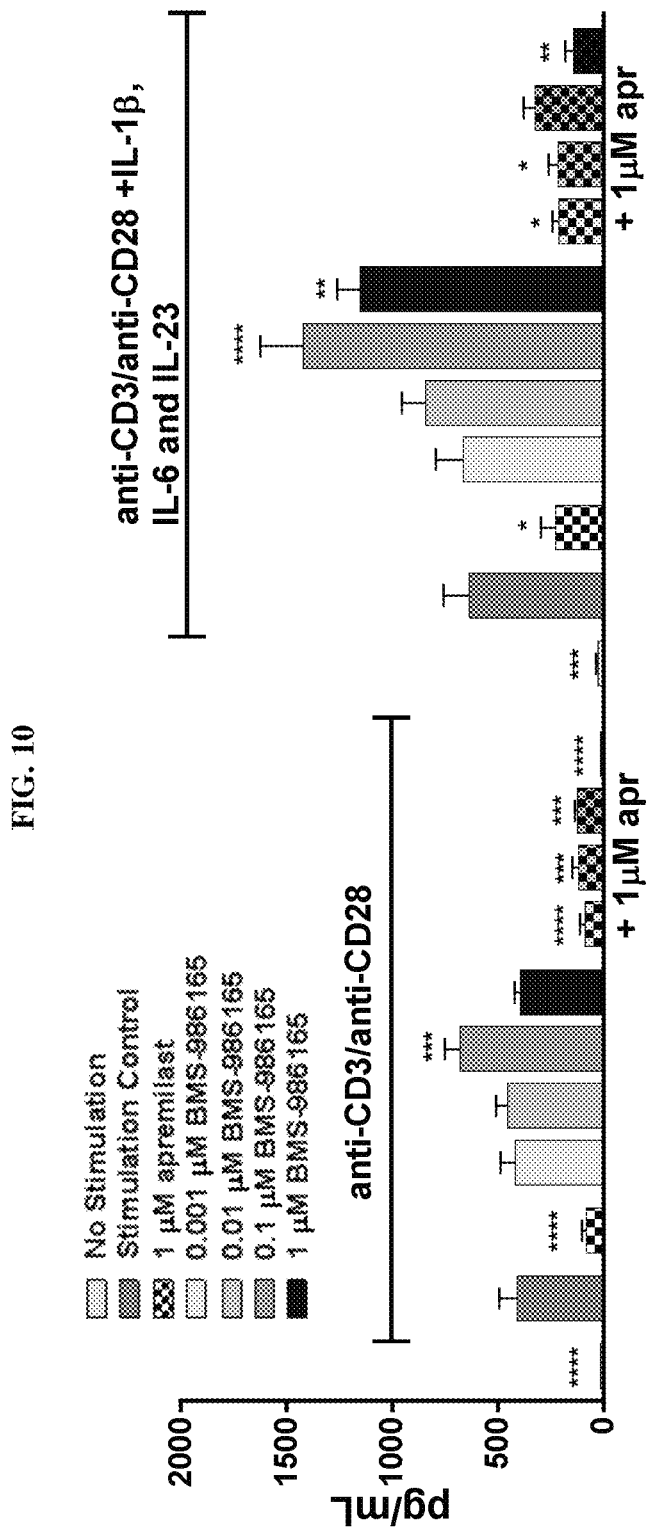
FIG. 10 illustrates granulocyte-macrophage colony-stimulating factor (GM-CSF) cytokine production by apremilast and BMS-986165 in anti-CD3/anti-CD28 (Th0)

Granulocyte-Macrophage Colony-Stimulating Factor Cytokine Production by Apremilast and BMS-986165 in Anti-CD3/Anti-CD28 (Th0) or Anti-CD3/Anti-CD28, IL-1β, IL-6 and IL-23 (Th17) Stimulated Whole Blood Granulocyte-Macrophage Colony-Stimulating Factor (GM-CSF) cytokine expression results are in FIG. 9 and FIG. 10. GM-CSF cytokine expression was reduced 80% by apremilast under Th0 conditions and by 66% under Th17 conditions. BMS-986165 increased GM-CSF cytokine expression under both conditions. BMS-986165 increased GM-CSF by 19% at 0.001 µM, 36% at 0.01 µM, 110% at 0.1 µM and 31% at 1 µM in the Th0 conditions. When apremilast (0.1 µM) was added to BMS-986165 there was inhibition 60-80% of GM-CSF cytokine expression. In the Th17 stimulation BMS-986165 increased GM-CSF by 41% at 0.01 µM, 139% at 0.1 µM and 104% at 1 µM. When apremilast was added there was 40-73% inhibition of GM-CSF cytokine expression. Total pg/mL of GM-CSF in the Th0 and Th17 stimulation controls were 409 and 637 respectively. Apremilast significantly inhibited GM-CSF under both stimulation conditions. The increase of GM-CSF by BMS-986165 was significant at 0.1 µM (both Th0 and Th17) and 1 µM (Th17). The combination of apremilast and BMS-986165 significantly reduced GM-CSF cytokine levels at all concentrations and under both stimulation conditions.

Example 6

IL-23 Production in LPS Stimulated PBMCs with Apremilast and Tyk2i (BMS-986165) Treatment PBMCs from 9 healthy donors were analyzed for cytokine production in LPS stimulation condition (FIG. 11 to FIG. 17). Results in FIG. 11 and FIG. 12 showed the level of IL-23. FIG. 11 showed that Apremilast decreased IL-23 production in LPS stimulated PBMCs. IL-23 level from DMSO treated LPS stimulated PBMCs was set as 100% (control), cytokine levels were shown as normalized value in % compared to control. In contrast to decreasing IL-23 level by Apremilast, FIG. 12 showed that BMS-986165 induces IL-23 level in LPS stimulated PBMCs. At the range of 0.2 µM-2 µM, BMS-986165 induced a 20 fold increases of IL-23 compared to DMSO group. The combination of apremilast with BMS-986165 was able to decrease the induction of IL-23 by BMS-986165. With increased level of apremilast, there is significant reduction of IL-23 level. Statistical analysis using ANOVA and Turkey's multiple comparisons were performed to compare each treatment with BMS-986165 alone. There is significant reduction of IL-23 when combining BMS-986165 with low level of apremilast, which is at the concentration of 0.037 µM (**** $p<0.001$). When combined with 1 µM apremilast, the induction of IL-23 was 90% inhibited, and almost reached a similar level as apremilast alone. Thus, the curve of combination treatment with 1 µM apremilast has no significant difference compared to apremilast treatment alone.

Example 7

IL-12p40 Production in LPS Stimulated PBMCs with Apremilast and Tyk2i (BMS-986165) Treatment Results in FIG. 13 showed the normalized level of IL-12p40 compared to DMSO treated LPS stimulated PBMCs group. Apremilast decreased IL-12p40 in a dose dependent manner, whereas BMS-986165 increased it. The combination of BMS-986165 with apremilast significantly decreased the induction of IL-12p40 by BMS-986165. With 1 µM apremilast, the increased IL-12p40 induced by BMS-986165 was 85% inhibited, and almost reached a similar level as Apremilast alone. Statistical analysis using ANOVA and Turkey's multiple comparisons were performed to compare each treatment with BMS-986165 alone. **** $p<0.001$ Example 8

IL-12p70 Production in LPS Stimulated PBMCs with Apremilast and Tyk2i (BMS-986165) Treatment Results in FIG. 14 showed the normalized level of IL-12p70 compared to DMSO treated LPS stimulated PBMCs group. Apremilast decreased IL-12p70 in a dose dependent manner, whereas BMS-986165 increased it. The combination of BMS-986165 with apremilast significantly decreased the induction of IL-12p70 by BMS-986165. In combination treatment, both 0.3 µM and 1 µM significantly reduced IL-12p70 level induced by BMS-986165 and have no significant difference compared to apremilast alone. Statistical analysis using ANOVA and Turkey's multiple comparisons were performed to compare each treatment with BMS-986165 alone. **** $p<0.001$ Example 9

TNF-α Production in LPS Stimulated PBMCs with Apremilast and Tyk2i (BMS-986165) Treatment Results in FIG. 15 showed the normalized level of TNF-α compared to DMSO treated LPS stimulated PBMCs group. Apremilast decreased TNF-α level in a dose dependent manner, however, BMS-986165 induced 1.2-1.5 fold increase of TNF-α. The combination of BMS-986165 and apremilast significantly decreased the level of TNF-α. Statistical analysis using ANOVA and Turkey's multiple comparisons were performed to compare each treatment with BMS-986165 alone. **** $p<0.001$ Example 10

IFN-γ Production in LPS Stimulated PBMCs with Apremilast and Tyk2i (BMS-986165) Treatment Results in FIG. 16 showed the normalized level of IFN-γ compared to DMSO treated LPS stimulated PBMCs group. Both apremilast alone and BMS-986165 alone decreased IFN-γ in a dose dependent manner. The combination of BMS-986165 and apremilast has synergistic effect in reducing IFN-γ level which significantly decreased IFN-γ level compared to single compound treatment. Statistical analysis using ANOVA and Turkey's multiple comparisons were performed to compare each treatment with BMS-986165 alone. **** p<0.001.

Example 11

MCP-1 Production in LPS Stimulated PBMCs with Apremilast and Tyk2i (BMS-986165) Treatment Results in FIG. 17 showed the normalized level of MCP-1 compared to DMSO treated LPS stimulated PBMCs group. Both apremilast alone and BMS-986165 alone decreased MCP-1 in a dose dependent manner. The combination of BMS-986165 and Apremilast has synergistic effect in reducing MCP-1 level. Statistical analysis using ANOVA and Turkey's multiple comparisons were performed to compare each treatment with BMS-986165 alone. **** p<0.001.

Data Summary

Table 5 below provides a summary of the cytokine effects of apremilast and BMS-986165 on stimulated whole blood in the Ex-Vivo TruCulture® Assay. Synergistic effects are shown in bold and complementary effects are underlined.

Four healthy donors' whole blood was tested in the Tru-culture assay in Th0 (anti-CD3/anti-CD28) or Th17 (anti-CD3/anti-CD28+IL-1β, IL-6 and IL-23) conditions for 48 hours with the Tyk2 inhibitor BMS-986165+/−apremilast. BMS-986165 inhibited IL-17A, IL-17F, and IL-22 cytokine expression under Th0 and Th17 conditions. When combined with apremilast these cytokines were further reduced with a synergistic effect on IL-17A, IL-17F and IL-22 under Th17 conditions. BMS-986165 increased TNF-α and GM-CSF production, while apremilast inhibited production of these cytokines. When BMS-986165 was combined with apremilast there was a complementary effect on TNF-α and GM-CSF cytokine expression, with apremilast correcting the defect of BMS-986165. These combined effect provide means for treating diseases or disorders responsive to the inhibition of PDE4 such as for the treatment inflammatory diseases (e.g., psoriasis, psoriatic arthritis, and ulcerative colitis).

TABLE 5

| Stim. | Treatment | IL-17F % of Control | IL-17A % of Control | IL-22 % of Control | TNF-α % of Control | IL-23 % of Control | GM-CSF % of Control | IFN-γ % of Control | IL-10 % of Control |
|---|---|---|---|---|---|---|---|---|---|
| Th0 | 1 μM apremilast | 31.8 | 71.6 | 14.8 | 10.7 | 82.1 | 20.3 | 9.3 | 41.6 |
|  | 0.01 μM BMS-9896165 | 68.5 | 83.5 | 84.1 | 143.1 | 101.8 | 136.3 | 100.2 | 101.5 |
|  | 0.1 μM BMS-9896165 | 28.3 | 73.0 | 13.4 | 160.7 | 89.9 | 210.5 | 80.9 | 33.8 |
|  | 0.01 μM BMS-9896165 + apr | 33.8 | 84.0 | 11.2 | <u>13.5</u> | 79.3 | <u>27.4</u> | 12.2 | 42.0 |
|  | 0.1 μM BMS-9896165 + apr | 21.0 | 90.0 | 9.3 | <u>21.9</u> | 77.0 | <u>41.6</u> | 12.9 | 34.8 |
| Th17 | 1 μM apremilast | 59.7 | 102.4 | 57.5 | 5.8 | 94.3 | 33.8 | 18.7 | 32.6 |
|  | 0.01 μM BMS-9896165 | 73.6 | 97.7 | 83.3 | 118.5 | 93.8 | 141.1 | 114.2 | 78.4 |
|  | 0.1 μM BMS-9896165 | 30.0 | 79.2 | 39.8 | 177.4 | 96.3 | 239.3 | 74.7 | 46.6 |
|  | 0.01 μM BMS-9896165 + apr | 34.1 | 76.1 | 39.5 | <u>6.7</u> | 92.7 | <u>37.8</u> | 16.8 | 29.9 |
|  | 0.1 μM BMS-9896165 + apr | 11.5 | 66.1 | 9.2 | <u>8.2</u> | 84.2 | <u>60.8</u> | 8.4 | 45.4 |

| Stim. | Treatment | CCL20 % of Control | IL-13 % of Control | IL-1β % of Control | IL-2 % of Control | IL-21 % of Control | IL-4 % of Control | IL-5 % of Control | IL-6 % of Control |
|---|---|---|---|---|---|---|---|---|---|
| Th0 | 1 μM apremilast | 59.5 | 15.3 | 16.4 | 17.9 | 62.9 | 30.3 | 6.2 | 52.8 |
|  | 0.01 μM BMS-9896165 | 82.7 | 146.9 | 113.5 | 120.1 | 107.6 | 122.8 | 153.1 | 149.3 |
|  | 0.1 μM BMS-9896165 | 106.4 | 205.9 | 113.2 | 187.4 | 94.5 | 114.7 | 178.6 | 124.0 |

TABLE 5-continued

|  |  |  |  |  |  |  |  |  |  |
|---|---|---|---|---|---|---|---|---|---|
|  | 0.01 µM BMS-9896165 + apr | 73.1 | 25.0 | 30.4 | 18.2 | 62.9 | 33.1 | 9.1 | 112.6 |
|  | 0.1 µM BMS-9896165 + apr | 97.0 | 45.1 | 41.6 | 22.9 | 68.9 | 37.6 | 16.6 | 210.0 |
| Th17 | 1 µM apremilast | 220.3 | 22.1 | 98 | 14.4 | 76.2 | 36.7 | 4.8 | 95.3 |
|  | 0.01 µM BMS-9896165 | 121.7 | 158.1 | 94.2 | 128.5 | 91.5 | 126.5 | 144.3 | 96.8 |
|  | 0.1 µM BMS-9896165 | 157.8 | 287.5 | 89.0 | 250.3 | 86.3 | 161.9 | 249.9 | 112.7 |
|  | 0.01 µM BMS-9896165 + apr | 270.3 | 26.1 | 88.7 | 15.9 | 72.8 | 27.4 | 6.4 | 108.9 |
|  | 0.1 µM BMS-9896165 + apr | 340.1 | 46.2 | 82.8 | 21.9 | 54.5 | 28.7 | 8.0 | 101.1 |

Table 6 below provides a summary of the cytokine effects of apremilast and BMS-986165 on LPS stimulated PBMCs. Arrows pointing up indicate induction and arrows pointing down indicate decrease of the production of cytokines.

PBMCs from 9 healthy donors were tested in LPS stimulated condition with or without BMS-986165 or apremilast or the combination of both. BMS-986165 treatment alone induced IL-23, IL-12p40, IL-12p70 and TNF-α, whereas apremilast treatment alone decreased these cytokines. When BMS-986165 was combined with apremilast, these cytokines were either unchanged or reduced compared to DMSO control group. These results indicate that apremilast could inhibit the induction of these cytokines by BMS-986165. Both apremilast and BMS-986165 reduced IFN-γ and MCP-1 production, and the combination of both further reduced these two cytokines with a synergistic effect. BMS-986165 inhibits Th17 lineage cytokines, which provide a means for treating diseases where Th17 cytokines are implicated in the pathogenesis. However, the induction of some proinflammatory cytokines, such as IL-23, IL-12 and TNF-α, by BMS-986165 could be a disadvantage in disease treatment. The combined effects of apremilast and BMS-986165 in which IL-23, IL-12 and TNF-α were decreased showed an advantage of combining these two compounds in treating inflammatory diseases such as psoriasis, psoriatic arthritis, and ulcerative colitis.

The invention claimed is:
1. A method of treating a disease or disorder in a human subject, comprising administering to the human subject from about 10 mg/day to about 60 mg/day of N-[2-[(1S)-1-(3-ethoxy-4-methoxyphenyl)-2-(methylsulfonyl)ethyl]-2,3-dihydro-1,3-dioxo-1H-isoindol-4-yl]acetamide, or a pharmaceutically acceptable salt thereof; and from about 2 mg/day to about 14 mg/day of a tyrosine kinase 2 (Tyk2) inhibitor of the formula:

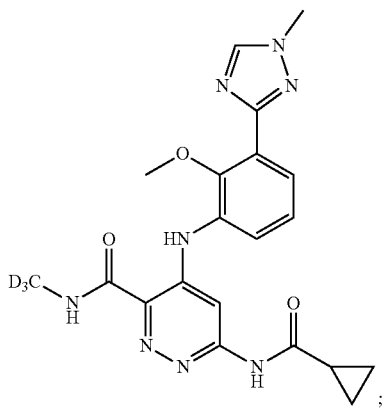 [SMILES: [2H]C([2H])([2H])NC(=O)c1nnc(NC(=O)C2CC2)cc1Nc1cccc(-c2ncn(C)n2)c1OC]

TABLE 6

|  | Viability | IL-23 | IL-12p40 | IL-12p70 | TNF-α | IFNγ | MCP-1 | GM-CSF | G-CSF | IL-1β | IL-1ra |
|---|---|---|---|---|---|---|---|---|---|---|---|
| Apremilast | — | ↓ | ↓ | ↓ | ↓ | ↓ | ↓ | ↓ | ↑ | — | — |
| BMS-986165 | — | ↑↑ | ↑ | ↑ | ↑ | ↓ | ↓ | ↑ | ↑ | — | ↓ |
| Combination | — | — | ↓ | — | ↓ | ↓↓ | ↓↓ | ↑ | ↑ | — | ↓ |

|  | IL-2 | IL-4 | IL-5 | IL-6 | IL-10 | IL-13 | IL-15 | IL-17 | IL-22 | IFN α2 | IFS Nβ |
|---|---|---|---|---|---|---|---|---|---|---|---|
| Apremilast | ↓ | — | — | — | ↑ | — | — | — | — | — | — |
| BMS-986165 | — | — | — | — | — | ↑ | — | — | — | — | — |
| Combination | ↓ | — | — | — | ↑ | — | — | — | — | — | — |

↑ Induced
— No change
↓ Reduced or a pharmaceutically acceptable salt thereof, wherein the disease or disorder is selected from chronic obstructive pulmonary disease, asthma, chronic pulmonary inflammatory disease, hyperoxic alveolar injury, inflammatory skin disease, psoriasis, psoriatic arthritis, rheumatoid arthritis, rheumatoid spondylitis, atopic dermatitis, depression, osteoarthritis, contact dermatitis, ankylosing spondylitis, lupus, lupus nephritis, cutaneous lupus erythematosus, systemic lupus erythrematosus, erythema nodosum leprosum, Sjögren's syndrome, inflammatory bowel disease, Crohn's Disease, Behçet's Disease, and ulcerative colitis.

2. The method of claim 1, wherein the N-[2-[(1S)-1-(3-ethoxy-4-methoxyphenyl)-2-(methylsulfonyl)ethyl]-2,3-dihydro-1,3-dioxo-1H-isoindol-4-yl]acetamide is greater than 95% stereomerically pure.

3. The method of claim 1, wherein the N-[2-[(1S)-1-(3-ethoxy-4-methoxyphenyl)-2-(methylsulfonyl)ethyl]-2,3-dihydro-1,3-dioxo-1H-isoindol-4-yl]acetamide is greater than 99% stereomerically pure.

4. The method of claim 1, wherein the subject is administered about 30 mg per day or about 60 mg per day of N-[2-[(1S)-1-(3-ethoxy-4-methoxyphenyl)-2-(methylsulfonyl)ethyl]-2,3-dihydro-1,3-dioxo-1H-isoindol-4-yl]acetamide, or a pharmaceutically acceptable salt thereof.

5. The method of claim 1, wherein the subject is administered about 30 mg of N-[2-[(1S)-1-(3-ethoxy-4-methoxyphenyl)-2-(methylsulfonyl)ethyl]-2,3-dihydro-1,3-dioxo-1H-isoindol-4-yl]acetamide once daily.

6. The method of claim 1, wherein the subject is administered about 30 mg of N-[2-[(1S)-1-(3-ethoxy-4-methoxyphenyl)-2-(methylsulfonyl)ethyl]-2,3-dihydro-1,3-dioxo-1H-isoindol-4-yl]acetamide twice daily.

7. The method of claim 1, wherein the N-[2-[(1S)-1-(3-ethoxy-4-methoxyphenyl)-2-(methylsulfonyl)ethyl]-2,3-dihydro-1,3-dioxo-1H-isoindol-4-yl]acetamide is formulated as part of a pharmaceutical composition comprising a pharmaceutically acceptable carrier.

8. The method of claim 7, wherein the N-[2-[(1S)-1-(3-ethoxy-4-methoxyphenyl)-2-(methylsulfonyl)ethyl]-2,3-dihydro-1,3-dioxo-1H-isoindol-4-yl]acetamide is administered orally.

9. The method of claim 7, wherein the N-[2-[(1S)-1-(3-ethoxy-4-methoxyphenyl)-2-(methylsulfonyl)ethyl]-2,3-dihydro-1,3-dioxo-1H-isoindol-4-yl]acetamide is administered orally in the form of a tablet or a capsule.

10. The method of claim 1, wherein the disease or disorder is psoriasis.

11. The method of claim 1, wherein the disease or disorder is plaque psoriasis.

12. The method of claim 1, wherein the disease or disorder is moderate to severe plaque psoriasis.

13. The method of claim 10, wherein the human subject is a candidate for phototherapy or systematic therapy.

14. The method of claim 1, wherein the disease or disorder is psoriatic arthritis.

15. The method of claim 1, wherein the human subject is administered from about 3 mg/day to about 12 mg/day of the Tyk2 inhibitor.

16. The method of claim 1, wherein the human subject is administered about 4 mg/day, about 6 mg/day, or about 12 mg/day of the Tyk2 inhibitor.

17. The method of claim 1, wherein the human subject is administered about 4 mg/day of the Tyk2 inhibitor.

18. The method of claim 1, wherein the human subject is administered about 6 mg/day of the Tyk2 inhibitor.

19. The method of claim 1, wherein the human subject is administered about 12 mg/day of the Tyk2 inhibitor.

20. The method of claim 1, wherein the human subject is administered about 20 mg/day, about 40 mg/day, or about 60 mg/day N-[2-[(1S)-1-(3-ethoxy-4-methoxyphenyl)-2-(methylsulfonyl)ethyl]-2,3-dihydro-1,3-dioxo-1H-isoindol-4-yl]acetamide.

\* \* \* \* \*